United States Patent
Ruggeri et al.

(10) Patent No.: US 7,618,996 B2
(45) Date of Patent: Nov. 17, 2009

(54) DIARYL ETHER DERIVATIVES AND USES THEREOF

(75) Inventors: Roger B. Ruggeri, Waterford, CT (US); George T. Magnus-Aryitey, Ledyard, CT (US)

(73) Assignee: Pfizer Inc., New York, NY (US)

( * ) Notice: Subject to any disclaimer, the term of this patent is extended or adjusted under 35 U.S.C. 154(b) by 53 days.

(21) Appl. No.: 11/852,358

(22) Filed: Sep. 10, 2007

(65) Prior Publication Data

US 2008/0070887 A1 Mar. 20, 2008

Related U.S. Application Data

(60) Provisional application No. 60/824,944, filed on Sep. 8, 2006.

(51) Int. Cl.
*A61K 31/35* (2006.01)
*A61K 31/165* (2006.01)
*C07C 237/00* (2006.01)
*C07D 315/00* (2006.01)

(52) U.S. Cl. .................. 514/451; 514/617; 564/183; 549/426

(58) Field of Classification Search ................ 560/115; 549/427, 426; 546/335; 514/451, 617; 564/183
See application file for complete search history.

(56) References Cited

U.S. PATENT DOCUMENTS

| | | | |
|---|---|---|---|
| 2003/0096844 A1* | 5/2003 | Kozlowski et al. | 514/332 |
| 2003/0191156 A1 | 10/2003 | Stucky et al. | 514/334 |
| 2005/0222204 A1 | 10/2005 | Mitch et al. | 514/317 |
| 2006/0166987 A1 | 7/2006 | Benesh et al. | 514/235.51 |
| 2006/0205715 A1 | 9/2006 | Pedregal-Tercero et al. | 514/221 |
| 2006/0217372 A1 | 9/2006 | Blanco-Pillado et al. | 514/227.5 |
| 2007/0010558 A1 | 1/2007 | Benesh et al. | 514/342 |
| 2007/0066658 A1 | 3/2007 | Chappel | 564/338 |
| 2007/0112036 A1 | 5/2007 | De La Torre et al. | 514/341 |
| 2007/0179129 A1 | 8/2007 | Diaz et al. | 514/217.03 |
| 2007/0287751 A1 | 12/2007 | De La Torre et al. | 514/620 |

FOREIGN PATENT DOCUMENTS

| | | |
|---|---|---|
| EP | 0827746 | 8/1997 |
| EP | 0921120 | 2/1998 |
| WO | WO2007047397 | 4/2007 |

OTHER PUBLICATIONS

Hadcock, et al., Role of opiates and their receptors in the regulation of food intake and body weight. *Drug Discovery Today; Therapeutic Strategies* (2005), vol. 2(2), pp. 171-175.

Manzanares, et al., Interactions between cannabinoid and opioid receptor systems in the mediation of ethanol effects. *Alcohol and Alcoholism* (Oxford, United Kingdom) (2005), vol. 40(1), pp. 25-34.

Marriott, et al., Synthesis of the farnesyl ether 2,3,5-trifuoro-6-hydroxy-4-[(E,E)-3,7,11-trimethyldodeca-2,6,10-trien-1-yloxy]nitrobenzene, and related compounds containing a substituted . . . , *Journal of Chemistry Society*, (2000), Perkin Trans 1, pp. 4265-4278.

Shuker, et al., The application of high-throughput synthesis and purification to the preparation of ethanolamines. *Tetrahedron Letters* (1997), vol. 38(35), pp. 6149-6152.

* cited by examiner

*Primary Examiner*—Janet L Andres
*Assistant Examiner*—Binta M Robinson
(74) *Attorney, Agent, or Firm*—Gregg C. Benson; Lisa A. Samuels

(57) ABSTRACT

Compounds of Formula (I) that act as antagonists at the mu, kappa and/or delta opioid receptors and therefore useful in the treatment of diseases, conditions and/or disorders that benefit from such antagonism in animals are described herein.

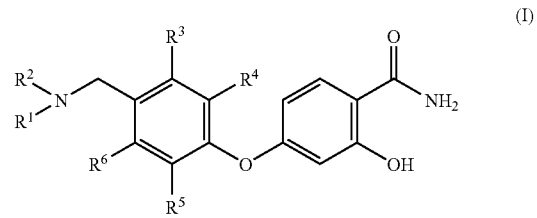

(I)

where $R^1$, $R^2$, $R^3$, $R^4$, $R^5$, and $R^6$ are described herein.

16 Claims, No Drawings

DIARYL ETHER DERIVATIVES AND USES THEREOF

FIELD OF THE INVENTION

The present invention relates to diaryl ether derivatives and the uses thereof for treating diseases, conditions and/or disorders mediated by the opioid receptors. The compounds are particularly useful as mu, kappa, and delta ($\mu$, $\kappa$, and $\delta$) opioid receptor antagonists.

BACKGROUND

Obesity is a significant health problem due to its serious medical complications that include co-morbidities such as hypertension, insulin resistance, diabetes, coronary artery disease and heart failure (collectively referred to as Metabolic Syndrome). Obesity and its related co-morbidities continue to cause rising health issues in the developed world and are beginning to affect the developing world as well. The negative health consequences of obesity make it the second leading cause of preventable death in the United States and impart a significant economic and psychosocial effect on society. See, McGinnis M, Foege W H., "Actual Causes of Death in the United States," *JAMA*, 270, 2207-12 (1993). Clearly, there is a need to identify and develop new medications that treat and/or prevent obesity and its associated co-morbidities.

Although the clinical data using naltrexone have been inconsistent, there is considerable evidence in the literature implicating opioid receptors in the regulation of energy homeostasis, suggesting that antagonism of one or more of the opiate receptor subtypes can be a suitable target for the treatment of obesity. See, e.g., Hadcock, J. R., et al., "Role of opiates and their receptors in the regulation of food intake and body weight," *Drug Discovery Today: Therapeutic Strategies*, 2(2), 171-175 (2005).

Pan-selective opioid receptor antagonists (e.g., LY255582) have been shown to provide robust anorectic effects. See, e.g., Gackenheimer, S. L., et al., "Localization of opioid receptor antagonist [$^3$H]-LY255582 binding sites in mouse brain: Comparison with the distribution of mu, delta and kappa binding sites," *Neuropeptide*, 39, 559-567 (2005): Shaw, W. N, et al., "The effect of the opioid antagonist LY255582 on body weight of the obese Zucker rat," *Int J Obes*, 15(6), 387-95 (1991): Shaw, W. N., "Long-term treatment of obese Zucker rats with LY255582 and other appetite suppressants," *Pharmacol Biochem Behav*, 46(3), 653-9 (1993): and Levine, A. S., et al., "Central administration of the opioid antagonist, LY255582, decreases short- and long-term food intake in rats," *Brain Res*, 566(1-2), 193-7 (1991). Compounds that act as inverse agonists or antagonist at the mu-, kappa- and delta-opioid receptors have also been reported. In particular, LY515300 (3,4-dimethyl-4-(3-hydroxyphenyl)piperidine) has been shown to have sub-nanomolar binding affinity for the mu- and kappa-opioid receptor subtypes, but has a lower affinity for the delta-opioid receptor. See, e.g., Statnick, M. A., et al., "Na$^+$-dependent high affinity binding of [3H] LY515300, a 3,4-dimethyl-4-(3-hydroxyphenyl)piperidine opioid receptor inverse agonist," *Eur J Pharm*, 482, 139-150 (2003): and Zimmerman, D. M., et al., "Structure-activity relations of trans-3,4-dimethyl-4-(3-hydroxyphenyl)piperidine antagonists for mu- and kappa-opioid receptor," *J Med Chem* 36(20), 2833-2841 (1993).

Diaryl ethers that act as opioid receptor antagonists are described in Shuker, A. J., et al., "The Application of High-Throughput Synthesis and Purification to the Preparation of Ethanolamines" *Tetra Lett*, 38(35), 6149-6152 (1997); and PCT Publication Nos. WO 04/026305, WO 04/080968, WO 04/080996, WO 05/061442, WO 05/066164, WO 05/090286, WO 05/090337 and WO 05/092836.

Although many opioid receptor antagonists are known, there remains a need to identify compounds having improved efficacy and therapeutic indices, in particular for the treatment of obesity and obesity-related co-morbidities.

SUMMARY

Compounds of Formula (I) have been found to act as antagonists at the mu, kappa and/or delta opioid receptors and therefore may be used in the treatment of diseases, conditions and/or disorders that benefit from such antagonism (e.g., diseases related to obesity and obesity-related co-morbidities). In particular, the compounds of Formula (I) provide combined mu and kappa receptor antagonism resulting in improved food intake efficacy, and potency.

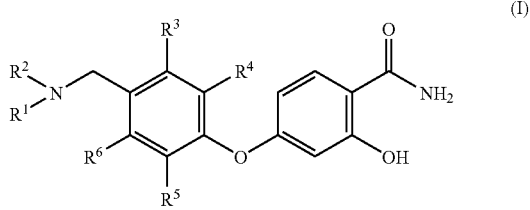

wherein $R^1$ is hydrogen or methyl; $R^2$ is ($C_3$-$C_{10}$)alkyl, a 5-6 membered cycloalkyl optionally fused to a benzene ring, or the group —$(CH(R))_m(CH_2)_n$-A [where: m is 1; n is 0, 1 or 2; R is hydrogen, methyl or ethyl; and A is ($C_1$-$C_4$)alkoxy, phenoxy, phenyl, 3-8 membered cycloalkyl, 5-6 membered heterocycle containing 1 to 2 heteroatoms independently selected from O, N, or S, or 5-6 membered heteroaryl containing 1 to 3 heteroatoms independently selected from O, S, or N, and where said phenyl, said cycloalkyl, said heterocycle, and said heteroaryl are optionally fused to a benzene ring or optionally substituted with one to three substituents independently selected from —OH, halo, ($C_1$-$C_4$)alkyl, —$CF_3$, —$OCF_3$, ($C_1$-$C_4$)alkoxy, CN, acetylamino, or phenoxy]; $R^3$ is hydrogen; $R^4$ is hydrogen or halo (F, Cl, Br or I, preferably, F or Cl, more preferably F); $R^5$ is hydrogen or halo (F, Cl, Br or I, preferably, F or Cl, more preferably F); and $R^6$ is hydrogen; or a pharmaceutically acceptable salt thereof.

DEFINITIONS

As used herein, the term "alkyl" refers to a hydrocarbon radical of the general formula $C_nH_{2n+1}$. The alkane radical may be straight or branched. For example, the term "($C_1$-$C_6$) alkyl" refers to a monovalent, straight, or branched aliphatic group containing 1 to 6 carbon atoms (e.g., methyl, ethyl, n-propyl, i-propyl, n-butyl, i-butyl, s-butyl, t-butyl, n-pentyl, 1-methylbutyl, 2-methylbutyl, 3-methylbutyl, neopentyl, 3,3-dimethylpropyl, hexyl, 2-methylpentyl, and the like). Similarly, the alkyl portion (i.e., alkyl moiety) of an alkoxy, acyl (e.g., alkanoyl), alkylamino, dialkylamino, and alkylthio group have the same definition as above. When indicated as being "optionally substituted", the alkane radical or alkyl moiety may be unsubstituted or substituted with one or more substituents (generally, one to three substituents except in the case of halogen substituents such as perchloro or perfluoroalkyls) independently selected from the group of substituents listed below in the definition for "substituted." "Halo-substituted alkyl" refers to an alkyl group substituted with one or more halogen atoms (e.g., fluoromethyl, difluoromethyl, trifluoromethyl, perfluoroethyl, and the like).

The term "cycloalkyl" refers to nonaromatic rings that are fully hydrogenated and may exist as a single ring, bicyclic ring or a spiral ring. Unless specified otherwise, the carbocyclic ring is generally a 3- to 8-membered ring. For example, cycloalkyl include groups such as cyclopropyl, cyclobutyl, cyclopentyl, cyclohexyl, cyclohexenyl, norbornyl (bicyclo [2.2.1]heptyl), bicyclo[2.2.2]octyl, and the like. When designated as being "optionally substituted", the cycloalkyl group may be unsubstituted or substituted with one or more substituents (typically, one to three substituents) independently selected from the group of substituents listed below in the definition for "substituted." A substituted carbocyclic ring also includes groups wherein the carbocyclic ring is fused to a phenyl ring (e.g., indanyl). The carbocyclic group may be attached to the chemical entity or moiety by any one of the carbon atoms within the carbocyclic ring system.

The term "heterocycle" refers to nonaromatic rings that are fully hydrogenated and may exist as a single ring, bicyclic ring or a spiral ring. Unless specified otherwise, the heterocyclic ring is generally a 3- to 6-membered ring containing 1 to 3 heteroatoms (preferably 1 or 2 heteroatoms) independently selected from sulfur, oxygen and/or nitrogen. Heterocyclic rings include groups such as epoxy, aziridinyl, tetrahydrofuranyl, pyrrolidinyl, N-methylpyrrolidinyl, piperidinyl, piperazinyl, pyrazolidinyl, 4H-pyranyl, morpholino, thiomorpholino, tetrahydrothienyl, tetrahydrothienyl 1,1-dioxide, and the like. When indicated as being "optionally substituted", the heterocycle group may be unsubstituted or substituted with one or more substituents (typically, one to three substituents) independently selected from the group of substituents listed below in the definition for "substituted." A substituted heterocyclic ring includes groups wherein the heterocyclic ring is fused to an aryl or heteroaryl ring (e.g., 2,3-dihydrobenzofuranyl, 2,3-dihydroindolyl, 2,3-dihydrobenzothiophenyl, 2,3-dihydrobenzothiazolyl, etc.). When substituted, the heterocycle group is preferably substituted with 1 or 2 substituents. The heterocyclic group may be attached to the chemical entity or moiety by any one of the ring atoms within the heterocyclic ring system.

The term "aryl" or "aromatic carbocyclic ring" refers to aromatic moieties having a single (e.g., phenyl) or a fused ring system (e.g., naphthalene, anthracene, phenanthrene, etc.). A typical aryl group is a 6- to 10-membered aromatic carbocyclic ring(s). When indicated as being "optionally substituted", the aryl groups may be unsubstituted or substituted with one or more substituents (preferably no more than three substituents). Substituted aryl groups include a chain of aromatic moieties (e.g., biphenyl, terphenyl, phenylnaphthalyl, etc.). When substituted, the aromatic moieties are preferably substituted with 1 or 2 substituents. The aryl group may be attached to the chemical entity or moiety by any one of the carbon atoms within the aromatic ring system. Similarly, the aryl portion (i.e., aromatic moiety) of an aryloxy has the same definition as above.

The term "heteroaryl" or "heteroaromatic ring" refers to aromatic moieties containing at least one heteroatom (e.g., oxygen, sulfur, nitrogen or combinations thereof) within a 5- to 10-membered aromatic ring system (e.g., pyrrolyl, pyridyl, pyrazolyl, indolyl, indazolyl, thienyl, furanyl, benzofuranyl, oxazolyl, imidazolyl, tetrazolyl, triazinyl, pyrimidyl, pyrazinyl, thiazolyl, purinyl, benzimidazolyl, quinolinyl, isoquinolinyl, benzothiophenyl, benzoxazolyl, etc.). The heteroaromatic moiety may consist of a single or fused ring system. A typical single heteroaryl ring is a 5- to 6-membered ring containing one to three heteroatoms independently selected from oxygen, sulfur and nitrogen and a typical fused heteroaryl ring system is a 9- to 10-membered ring system containing one to four heteroatoms independently selected from oxygen, sulfur and nitrogen. When indicated as being "optionally substituted", the heteroaryl groups may be unsubstituted or substituted with one or more substituents (preferably no more than three substituents). The heteroaryl group may be attached to the chemical entity or moiety by any one of the atoms within the aromatic ring system (e.g., imidazol-1-yl, imidazol-2-yl, imidazol-4-yl, imidazol-5-yl, pyrid-2-yl, pyrid-3-yl, pyrid-4-yl, pyrid-5-yl, or pyrid-6-yl).

The term "substituted" specifically envisions and allows for one or more substitutions that are common in the art. However, it is generally understood by those skilled in the art that the substituents should be selected so as to not adversely affect the pharmacological characteristics of the compound or adversely interfere with the use of the medicament. In the case of substituted combinations, such as "substituted aryl $(C_1-C_6)$alkyl", either the aryl or the alkyl group may be substituted, or both the aryl and the alkyl groups may be substituted with one or more substituents (typically, one to three substituents except in the case of perhalo substitutions). An aryl or heteroaryl substituted carbocyclic or heterocyclic group may be a fused ring (e.g., indanyl, dihydrobenzofuranyl, dihydroindolyl, etc.).

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term "animal" refers to humans (male or female), companion animals (e.g., dogs, cats and horses), food-source animals, zoo animals, marine animals, birds and other similar animal species. "Edible animals" refers to food-source animals such as cows, pigs, sheep and poultry.

The phrase "pharmaceutically acceptable" indicates that the substance or composition must be compatible chemically and/or toxicologically, with the other ingredients comprising a formulation, and/or the mammal being treated therewith.

The terms "treating", "treat", or "treatment" embrace both preventative, i.e., prophylactic, and palliative treatment.

The terms "modulating opioid receptor activity" or "Opioid-mediated" refers to the activation or deactivation of the mu, kappa and/or delta opioid receptors.

The term "compounds of the present invention" (unless specifically identified otherwise) refer to compounds of Formula (I) and pharmaceutically acceptable salts of the compounds, as well as, all stereoisomers (including diastereomers and enantiomers), tautomers and isotopically labeled compounds.

DETAILED DESCRIPTION

In the compounds of Formula I, $R^1$ is preferably hydrogen, and $R^4$ and $R^5$ are preferably hydrogen or fluoro.

$R^2$ is preferably (i) $(C_4-C_{10})$alkyl; (ii) 5-6 membered cycloalkyl optionally fused to a benzene ring; (iii) —(CH (R))$_m$(CH$_2$)$_n$-A, where m is 1, n is 0, and A is a 3-6 membered cycloalkyl, pyridinyl, or 5-6 membered heterocycle containing 1 to 2 heteroatoms independently selected from O, S, or N, where the cycloalkyl and the heterocycle are optionally substituted with hydroxy; or (iv) —(CH(R))$_m$(CH$_2$)$_n$-A, where m is 1, n is 1, and A is (C$_1$-C$_4$)alkoxy, phenoxy, 3-6 membered cycloalkyl, or a 5-6 membered heterocycle containing 1 to 2 heteroatoms independently selected from O, S, or N.

A preferred compound is the free base or hydrochloride salt of 4-{4-[(2-cyclopropyl-ethylamino)-methyl]-2-fluoro-phenoxy}-2-hydroxy-benzamide.

Some of the compounds described herein may contain at least one chiral center; consequently, those skilled in the art will appreciate that all stereoisomers (e.g., enantiomers and diastereomers) of the compounds illustrated and discussed herein are within the scope of the present invention. In addition, tautomeric forms of the compounds are also within the scope of the present invention.

Another aspect of the present invention is a pharmaceutical composition that comprises (1) a compound of the present invention, and (2) a pharmaceutically acceptable excipient, diluent, or carrier. Preferably, the composition comprises a therapeutically effective amount of a compound of the present invention. The composition may also contain at least one additional pharmaceutical agent (described herein). Preferred agents include anti-obesity agents (described herein below).

In yet another embodiment of the present invention, a method for treating a disease, condition and/or disorder that is mediated by antagonizing the mu, kappa and/or delta opioid receptors in animals that includes the step of administering to an animal (preferably, a human) in need of such treatment a therapeutically effective amount of a compound of the present invention (or a pharmaceutical composition thereof), e.g., to reduce body weight, lower blood pressure, and lower insulin resistance.

Diseases, conditions, and/or disorders mediated by antagonizing the mu, kappa and/or delta opioid receptors include obesity (including weight control or weight maintenance), and obesity-related co-morbidities (e.g., dyslipidemia, hypertension, insulin resistance, diabetes, coronary artery disease and heart failure).

Compounds of the present invention may be administered in combination with other pharmaceutical agents. Preferred pharmaceutical agents include anti-obesity agents, such as apo-B/MTP inhibitors, Cannabinoid-1 (CB-1) antagonists (or inverse agonists), 11β-hydroxy steroid dehydrogenase-1 (11β-HSD type 1) inhibitors, peptide YY$_{3-36}$ (including analogs thereof), MCR-4 agonists, CCK-A agonists, monoamine reuptake inhibitors, sympathomimetic agents, β$_3$ adrenergic agonists, dopamine agonists, melanocyte-stimulating hormone analogs, 5-HT2c agonists, melanin concentrating hormone antagonists, leptin, leptin analogs, leptin agonists, galanin antagonists, lipase inhibitors, bombesin agonists, neuropeptide-Y antagonists (e.g., NPY Y5 antagonists such as those described herein below), thyromimetic agents, dehydroepiandrosterone or analogs thereof, glucocorticoid antagonists, orexin antagonists, glucagon-like peptide-1 agonists, ciliary neurotrophic factors, human agouti-related protein antagonists, ghrelin antagonists, histamine 3 antagonists or inverse agonists, and neuromedin U agonists, and the like.

The combination therapy may be administered as (a) a single pharmaceutical composition which comprises a compound of the present invention, at least one additional pharmaceutical agent described herein and a pharmaceutically acceptable excipient, diluent, or carrier; or (b) two separate pharmaceutical compositions comprising (i) a first composition comprising a compound of the present invention and a pharmaceutically acceptable excipient, diluent, or carrier, and (ii) a second composition comprising at least one additional pharmaceutical agent described herein and a pharmaceutically acceptable excipient, diluent, or carrier. The pharmaceutical compositions may be administered simultaneously or sequentially and in any order.

Compounds of the present invention may be synthesized by synthetic routes that include processes analogous to those well-known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-19, Wiley, New York (1967-1999 ed.), or *Beilsteins Handbuch der organischen Chemie*, 4, Aufl. ed. Springer-Verlag, Berlin, including supplements (also available via the Beilstein online database)).

For illustrative purposes, the reaction schemes depicted below provide potential routes for synthesizing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are depicted in the schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

In the preparation of compounds of the present invention, protection of remote functionality (e.g., primary or secondary amine) of intermediates may be necessary. The need for such protection will vary depending on the nature of the remote functionality and the conditions of the preparation methods. Suitable amino-protecting groups (NH-Pg) include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, *Protective Groups in Organic Synthesis*, John Wiley & Sons, New York, 1991.

Scheme I outlines the general procedures one could use to provide compounds of the present invention.

Scheme I

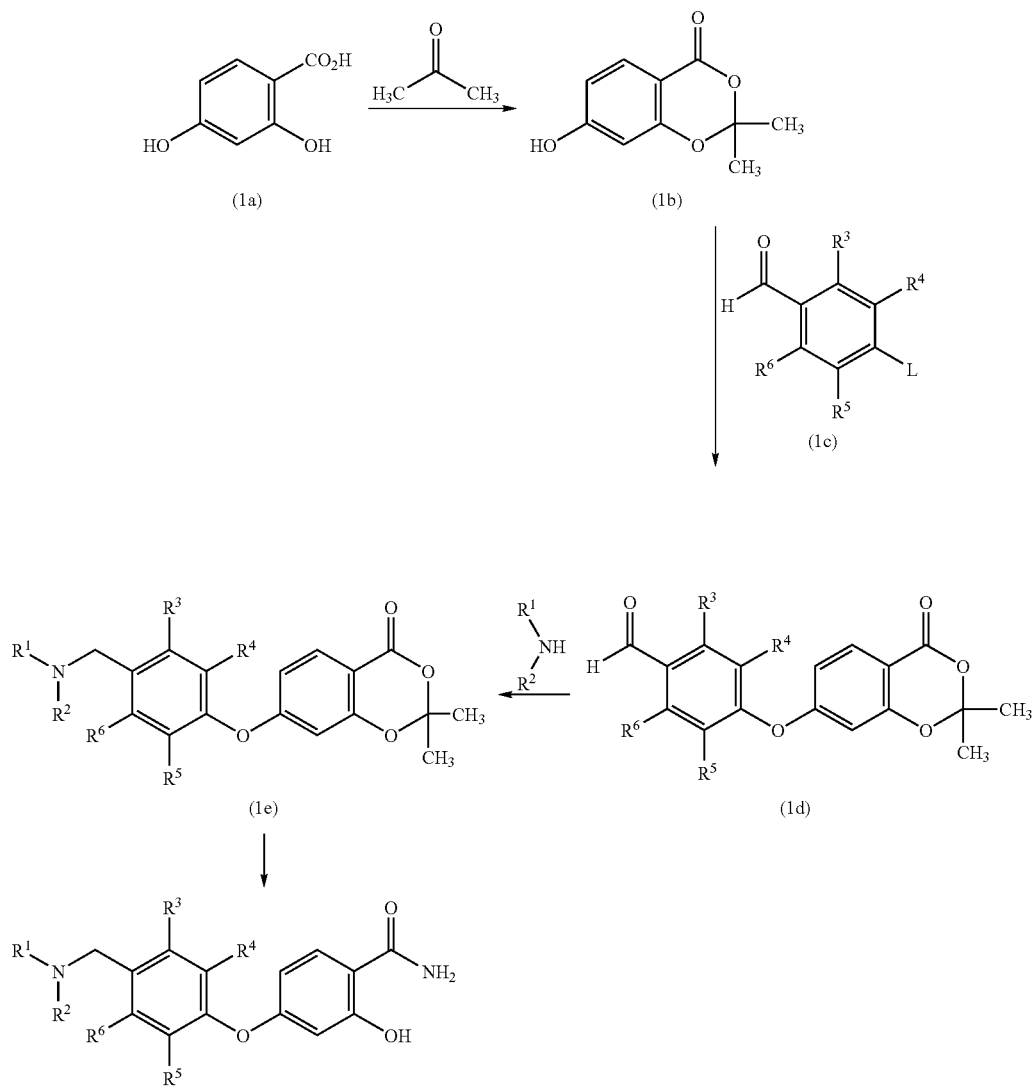

The 7-hydroxy-2,2-dimethyl-benzo[1,3]dioxin-4-one (1b) may be produced using the procedures described by Jonathan H. Marriott, et al., in *J. Chem Soc Perkin Trans* 1, 24, 4265-5278 (2000). For example, 2,4-dihydroxy-benzoic acid (1a) is treated with acetone in the presence of trifluoroacetic anhydride (TFAA) and trifluoroacetic acid (TFA) at about 0° C. to about room temperature. The desired benzaldehyde (1c), having the appropriate leaving group (L) at the linking position, is then condensed with 7-hydroxy-2,2-dimethyl-benzo[1,3]dioxin-4-one (1b) to form intermediate (1d). Suitable leaving groups include halo (e.g., fluoro, chloro or bromo) and sulfonate ester. Generally, the two components are heated together in the presence of a base (e.g., potassium carbonate) in a high boiling polar solvent (e.g., DMF). The aldehyde group is then converted into a benzylic amine by reductive amination to form the amino compound (1e). For example, the aldehyde intermediate (1d) is treated with the desired primary or secondary amine $(R^1(R^2)NH)$ in a protic solvent (e.g., ethanol). The reaction is then treated with a suitable hydride reducing agent (e.g., sodium borohydride, sodium triacetoxyborohydride or sodium cyanoborohydride) to form the amino compound (1e). The [1,3]dioxin-4-one functionality is then converted to an alpha-hydroxy amide by treating with ammonium hydroxide to form the final compound (I).

Alternatively, one could use the cyano equivalent to the benzaldehyde (1c). In this procedure, the nitrile is reduced with a suitable reducing agent (e.g., borane-tetrahydrofuran complex or sodium borohydride plus a transition metal salt (e.g., nickel chloride or cobalt chloride)) to form the benzylic amino intermediate (1e), where $R^1$ and $R^2$ are both hydrogen. The desired $R^2$ group may then be introduced via reduction amination with a desired aldehyde ($R^2C(O)H$) to form compound (I), where $R^1$ is hydrogen.

Those of skill in the art will realize that numerous alternative methods for making the diaryl ethers are also possible. For example, the procedures described in *Tetrahedron*, 56(29), 5045-5065 (2000); *Angewandte Chemie*, International Edition, 42(44), 5400-5449 (2003); and PCT Publication No. WO 01/072687.

Scheme II below illustrates an alternative synthesis for the compounds of the present invention when $R^1$ is hydrogen.

Scheme II

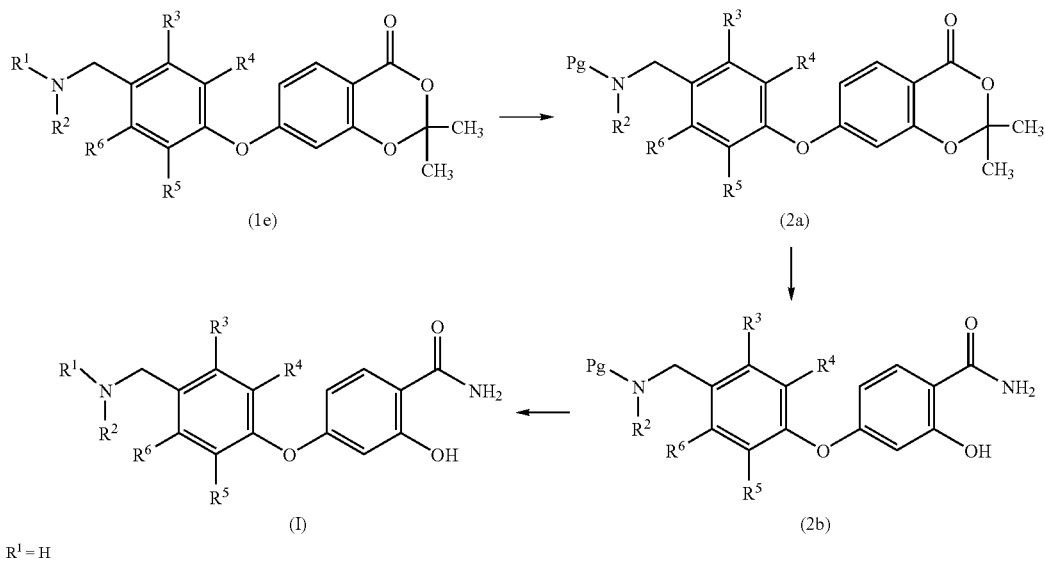

$R^1 = H$

When $R^1$ is hydrogen, it may be necessary to protect the secondary amino group with a protecting group (Pg) prior to formation of the alpha-hydroxy amide functionality. Once the amide is formed (intermediate (2b)), then the protecting group may be removed using conditions appropriate for the particular protecting group used. For example, when t-butoxycarbonyl (Boc) is used for the protecting group, then the group may be removed by treating with a strong acid (e.g., HCl). The acid salt of the compound of Formula (I) is formed which may be used as the salt or converted to the free base by treatment with an appropriate base.

The compounds of the present invention may be isolated and used per se or in the form of its pharmaceutically acceptable salt. The term "salts" refers to inorganic and organic salts of a compound of the present invention. These salts can be prepared in situ during the final isolation and purification of a compound, or by separately reacting the compound with a suitable organic or inorganic acid or base and isolating the salt thus formed. Representative salts include the hydrobromide, hydrochloride, hydroiodide, sulfate, bisulfate, nitrate, acetate, trifluoroacetate, oxalate, besylate, palmitate, pamoate, malonate, stearate, laurate, malate, borate, benzoate, lactate, phosphate, hexafluorophosphate, benzene sulfonate, tosylate, formate, citrate, maleate, fumarate, succinate, tartrate, naphthylate, mesylate, glucoheptonate, lactobionate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. See, e.g., Berge, et al., *J. Pharm. Sci.*, 66, 1-19 (1977).

The compounds of the present invention may contain asymmetric or chiral centers, and, therefore, exist in different stereoisomeric forms. It is intended that all stereoisomeric forms of the compounds of the present invention as well as mixtures thereof, including racemic mixtures, form part of the present invention. In addition, the present invention embraces all geometric and positional isomers. For example, if a compound of the present invention incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the present invention may be atropisomers (e.g., substituted biaryls) and are considered as part of this invention. Enantiomers can also be separated by use of a chiral HPLC column.

It is also possible that the intermediates and compounds of the present invention may exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. A specific example of a proton tautomer is the imidazole moiety where the proton may migrate between the two ring nitrogens. Valence tautomers include interconversions by reorganization of some of the bonding electrons.

The present invention also embraces isotopically-labeled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, sulfur, fluorine, iodine, and chlorine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{123}I$, $^{125}I$ and $^{36}Cl$, respectively.

Certain isotopically-labeled compounds of the present invention (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$, and $^{18}F$ are useful for positron emission tomography (PET) studies to examine substrate occupancy. Isotopically labeled compounds of the present invention can generally be prepared by following procedures analogous to those disclosed in the Schemes and/or in the Examples herein below, by substituting an isotopically labeled reagent for a non-isotopically labeled reagent.

Compounds of the present invention are useful for treating diseases, conditions and/or disorders modulated by the mu, kappa and/or delta opioid receptors; therefore, another embodiment of the present invention is a pharmaceutical composition comprising a therapeutically effective amount of a compound of the present invention and a pharmaceutically acceptable excipient, diluent or carrier. The compounds of the present invention (including the compositions and processes used therein) may also be used in the manufacture of a medicament for the therapeutic applications described herein.

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent)) is dissolved in a suitable solvent in the presence of one or more of the excipients described above. The compound of the present invention is typically formulated into pharmaceutical dosage forms to provide an easily controllable dosage of the drug and to give the patient an elegant and easily handleable product.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The present invention further provides a method of treating diseases, conditions and/or disorders modulated by the opioid receptor(s) in an animal that includes administering to an animal in need of such treatment a therapeutically effective amount of a compound of the present invention or a pharmaceutical composition comprising an effective amount of a compound of the present invention and a pharmaceutically acceptable excipient, diluent, or carrier. The method is particularly useful for treating diseases, conditions and/or disorders that benefit from antagonizing the mu, kappa and/or delta opioid receptors.

One aspect of the present invention is the treatment of obesity, and obesity-related disorders (e.g., overweight, weight gain, or weight maintenance).

Obesity and overweight are generally defined by body mass index (BMI), which is correlated with total body fat and estimates the relative risk of disease. BMI is calculated by weight in kilograms divided by height in meters squared ($kg/m^2$). Overweight is typically defined as a BMI of 25-29.9 $kg/m^2$, and obesity is typically defined as a BMI of 30 $kg/m^2$. See, e.g., National Heart, Lung, and Blood Institute, Clinical Guidelines on the Identification, Evaluation, and Treatment of Overweight and Obesity in Adults, The Evidence Report, Washington, D.C.: U.S. Department of Health and Human Services, NIH publication no. 98-4083 (1998).

Another aspect of the present invention is the treatment of obesity co-morbidities, such as metabolic syndrome. Metabolic syndrome includes diseases, conditions or disorders such as dyslipidemia, hypertension, insulin resistance, diabetes (e.g., Type 2 diabetes), coronary artery disease and heart failure. For more detailed information on Metabolic Syndrome, see, e.g., Zimmet, P. Z., et al., "The Metabolic Syndrome: Perhaps an Etiologic Mystery but Far From a Myth—Where Does the International Diabetes Federation Stand?," *Diabetes & Endocrinology*, 7(2), (2005); and Alberti, K. G., et al., "The Metabolic Syndrome—A New Worldwide Definition," *Lancet*, 366, 1059-62 (2005). Preferably, administration of the compounds of the present invention provides a statistically significant ($p<0.05$) reduction in at least one cardiovascular disease risk factor, such as lowering of plasma leptin, C-reactive protein (CRP) and/or cholesterol, as compared to a vehicle control containing no drug. The administration of compounds of the present invention may also provide a statistically significant ($p<0.05$) reduction in glucose serum levels.

For a normal adult human having a body weight of about 100 kg, a dosage in the range of from about 0.001 mg to about 10 mg per kilogram body weight is typically sufficient, preferably from about 0.01 mg/kg to about 5.0 mg/kg, more preferably from about 0.01 mg/kg to about 1 mg/kg. However, some variability in the general dosage range may be required depending upon the age and weight of the subject being treated, the intended route of administration, the particular compound being administered and the like. The determination of dosage ranges and optimal dosages for a particular patient is well within the ability of one of ordinary skill in the art having the benefit of the instant disclosure. It is also noted that the compounds of the present invention can be used in sustained release, controlled release, and delayed release formulations, which forms are also well known to one of ordinary skill in the art.

The compounds of this invention may also be used in conjunction with other pharmaceutical agents for the treatment of the diseases, conditions and/or disorders described herein. Therefore, methods of treatment that include administering compounds of the present invention in combination with other pharmaceutical agents are also provided. Suitable pharmaceutical agents that may be used in combination with the compounds of the present invention include anti-obesity agents.

Suitable anti-obesity agents include cannabinoid-1 (CB-1) antagonists (such as rimonabant), 11β-hydroxy steroid dehydrogenase-1 (11β-HSD type 1) inhibitors, MCR-4 agonists, cholecystokinin-A (CCK-A) agonists, monoamine reuptake inhibitors (such as sibutramine), sympathomimetic agents, $\beta_3$ adrenergic agonists, dopamine agonists (such as bromocriptine), melanocyte-stimulating hormone analogs, 5HT2c agonists, melanin concentrating hormone antagonists, leptin (the OB protein), leptin analogs, leptin agonists, galanin antagonists, lipase inhibitors (such as tetrahydrolipstatin, i.e. orlistat), anorectic agents (such as a bombesin agonist), neuropeptide-Y antagonists (e.g., NPY Y5 antagonists), $PYY_{3-36}$ (including analogs thereof), thyromimetic agents, dehydroepiandrosterone or an analog thereof, glucocorticoid agonists or antagonists, orexin antagonists, glucagon-like peptide-1 agonists, ciliary neurotrophic factors (such as Axokine™ available from Regeneron Pharmaceuticals, Inc., Tarrytown, N.Y. and Procter & Gamble Company, Cincinnati, Ohio), human agouti-related protein (AGRP) inhibitors, ghrelin antagonists, histamine 3 antagonists or inverse agonists, neuromedin U agonists, MTP/ApoB inhibitors (e.g., gut-selective MTP inhibitors, such as dirlotapide) and the like.

Preferred anti-obesity agents for use in the combination aspects of the present invention include CB-1 antagonists, gut-selective MTP inhibitors, CCKa agonists, 5HT2c agonists, $PYY_{1-36}$ (including analogs, such as pegylated PY $Y_{3-36}$), NPY Y5 antagonists, bromocriptine, orlistat, and sibutramine. Preferably, compounds of the present invention and combination therapies are administered in conjunction with exercise and a sensible diet.

Sibutramine can be prepared as described in U.S. Pat. No. 4,929,629; bromocriptine can be prepared as described in U.S. Pat. Nos. 3,752,814 and 3,752,888; orlistat can be prepared as described in U.S. Pat. Nos. 5,274,143; 5,420,305; 5,540,917; and 5,643,874; and $PYY_{3-36}$ (including analogs thereof) can be prepared as described in US Publication No. 2002/0141985 and WO 03/027637; and 5HT2c agonists can be prepared as described in U.S. Pat. No. 6,825,198.

Preferred CB-1 antagonists include: rimonabant (SR141716A also known under the tradename Acomplia™) is available from Sanofi-Synthelabo or can be prepared as described in U.S. Pat. No. 5,624,941; N-(piperidin-1-yl)-1-(2,4-dichlorophenyl)-5-(4-iodophenyl)-4-methyl-1H-pyrazole-3-carboxamide (AM251) is available from Tocris™, Ellisville, Mo.; [5-(4-bromophenyl)-1-(2,4-dichloro-phenyl)-4-ethyl-N-(1-piperidinyl)-1H-pyrazole-3-carboxamide] (SR147778) which can be prepared as described in U.S. Pat. No. 6,645,985; N-(piperidin-1-yl)-4,5-diphenyl-1-methylimidazole-2-carboxamide, N-(piperidin-1-yl)-4-(2,4-dichlorophenyl)-5-(4-chlorophenyl)-1-methylimidazole-2-carboxamide, N-(piperidin-1-yl)-4,5-di-(4-methylphenyl)-1-methylimidazole-2-carboxamide, N-cyclohexyl-4,5-di-(4-methylphenyl)-1-methylimidazole-2-carboxamide, N-(cyclohexyl)-4-(2,4-dichlorophenyl)-5-(4-chlorophenyl)-1-methylimidazole-2-carboxamide, and N-(phenyl)-4-(2,4-dichlorophenyl)-5-(4-chlorophenyl)-1-methylimidazole-2-carboxamide which can be prepared as described in PCT Publication No. WO 03/075660; the hydrochloride, mesylate and besylate salt of 1-[9-(4-chloro-phenyl)-8-(2-chloro-phenyl)-9H-purin-6-yl]-4-ethylamino-piperidine-4-carboxylic acid amide which can be prepared as described in U.S. Publication No. 2004/0092520; 1-[7-(2-chloro-phenyl)-8-(4-chloro-phenyl)-2-methyl-pyrazolo[1,5-a][1,3,5]triazin-4-yl]-3-ethylamino-azetidine-3-carboxylic acid amide and 1-[7-(2-chloro-phenyl)-8-(4-chloro-phenyl)-2-methyl-pyrazolo[1,5-a][1,3,5]triazin-4-yl]-3-methylamino-azetidine-3-carboxylic acid amide which can be prepared as described in U.S. Publication No. 2004/0157839; 3-(4-chloro-phenyl)-2-(2-chloro-phenyl)-6-(2,2-difluoro-propyl)-2,4,5,6-tetrahydro-pyrazolo[3,4-c]pyridin-7-one which can be prepared as described in U.S. Publication No. 2004/0214855; 3-(4-chloro-phenyl)-2-(2-chloro-phenyl)-7-(2,2-difluoro-propyl)-6,7-dihydro-2H,5H-4-oxa-1,2,7-triaza-azulen-8-one which can be prepared as described in U.S. Publication No. 2005/0101592; 2-(2-chloro-phenyl)-6-(2,2,2-trifluoro-ethyl)-3-(4-trifluoromethyl-phenyl)-2,6-dihydro-pyrazolo[4,3-d]pyrimidin-7-one which can be prepared as described in U.S. Publication No. 2004/0214838; (S)-4-chloro-N-{[3-(4-chloro-phenyl)-4-phenyl-4,5-dihydro-pyrazol-1-yl]-methylamino-methylene}-benzenesulfonamide (SLV-319) and (S)-N-{[3-(4-chloro-phenyl)-4-phenyl-4,5-dihydro-pyrazol-1-yl]-methylamino-methylene}-4-trifluoromethyl-benzenesulfonamide (SLV-326) which can be prepared as described in PCT Patent Application Publication No. WO 02/076949; N-piperidino-5-(4-bromophenyl)-1-(2,4-dichlorophenyl)-4-ethylpyrazole-3-carboxamide which can be prepared as described in U.S. Pat. No. 6,432,984; 1-[bis-(4-chloro-phenyl)-methyl]-3-[(3,5-difluoro-phenyl)-methanesulfonyl-methylene]-azetidine which can be prepared as described in U.S. Pat. No. 6,518,264; 2-(5-(trifluoromethyl)pyridin-2-yloxy)-N-(4-(4-chlorophenyl)-3-(3-cyanophenyl)butan-2-yl)-2-methylpropanamide which can be prepared as described in PCT Publication No. WO 04/048317; 4-{[6-methoxy-2-(4-methoxyphenyl)-1-benzofuran-3-yl]carbonyl}benzonitrile (LY-320135) which can be prepared as described in U.S. Pat. No. 5,747,524; 1-[2-(2,4-dichlorophenyl)-2-(4-fluorophenyl)-benzo[1,3]dioxole-5-sulfonyl]-piperidine which can be prepared as described in WO 04/013120; and [3-amino-5-(4-chlorophenyl)-6-(2,4-dichlorophenyl)-fluoro[2,3-b]pyridin-2-yl]-phenyl-methanone which can be prepared as described in PCT Publication No. WO 04/012671.

Preferred intestinal-acting MTP inhibitors include dirlotapide ((S)-N-{2-[benzyl(methyl)amino]-2-oxo-1-phenylethyl}-1-methyl-5-[4'-(trifluoromethyl)[1,1'-biphenyl]-2-carboxamido]-1H-indole-2-carboxamide) and 1-methyl-5-[(4'-trifluoromethyl-biphenyl-2-carbonyl)-amino]-1H-indole-2-carboxylic acid (carbamoyl-phenyl-methyl)-amide which can both be prepared using methods described in U.S. Pat. No. 6,720,351; (S)-2-[(4'-trifluoromethyl-biphenyl-2-carbonyl)-amino]-quinoline-6-carboxylic acid (pentylcarbamoyl-phenyl-methyl)-amide, (S)-2-[(4'-tert-butyl-biphenyl-2-carbonyl)-amino]-quinoline-6-carboxylic acid {[(4-fluoro-benzyl)-methyl-carbamoyl]-phenyl-methyl}-amide, and (S)-2-[(4'-tert-butyl-biphenyl-2-carbonyl)-amino]-quinoline-6-carboxylic acid [(4-fluoro-benzylcarbamoyl)-phenyl-methyl]-amide which can all be prepared as described in U.S. Publication No. 2005/0234099; (−)-4-[4-[4-[4-[[(2S, 4R)-2-(4-chlorophenyl)-2-[[(4-methyl-4H-1,2,4-triazol-3- yl)sulfanyl]methyl-1,3-dioxolan-4-yl]methoxy]phenyl]piperazin-1-yl]phenyl]-2-(1R)-1-methylpropyl]-2,4-dihydro-3H-1,2,4-triazol-3-one (also known as Mitratapide or R103757, also known under the tradename Yarvitan™) which can be prepared as described in U.S. Pat. Nos. 5,521,186 and 5,929,075; and implitapide (BAY 13-9952) which can be prepared as described in U.S. Pat. No. 6,265,431.

Most preferred is dirlotapide, mitratapide, (S)-2-[(4'-trifluoromethyl-biphenyl-2-carbonyl)-amino]-quinoline-6-carboxylic acid (pentylcarbamoyl-phenyl-methyl)-amide, (S)-2-[(4'-tert-butyl-biphenyl-2-carbonyl)-amino]-quinoline-6-carboxylic acid {[(4-fluoro-benzyl)-methyl-carbamoyl]-phenyl-methyl}-amide, or (S)-2-[(4'-tert-butyl-biphenyl-2-carbonyl)-amino]-quinoline-6-carboxylic acid [(4-fluoro-benzylcarbamoyl)-phenyl-methyl]-amide.

A preferred CCKa agonist includes N-benzyl-2-[4-(1H-indol-3-ylmethyl)-5-oxo-1-phenyl-4,5-dihydro-2,3,6,10b-tetraaza-benzo[e]azulen-6-yl]-N-isopropyl-acetamide which can be prepared as described in PCT Publication No. WO 2005/116034 or US Publication No. 2005-0267100 A1.

Preferred NPY Y5 antagonists include: 2-oxo-N-(5-phenylpyrazinyl)-spiro[isobenzofuran-1(3H),4'-piperidine]-1'-carboxamide which can be prepared as described in U.S. Publication No. 2002/0151456; and 3-oxo-N-(5-phenyl-2-pyrazinyl)-spiro[isobenzofuran-1 (3H), 4'-piperidine]-1'-carboxamide; 3-oxo-N-(7-trifluoromethylpyrido[3,2-b]pyridin-2-yl)-spiro-[isobenzofuran-1(3H), 4'-piperidine]-1'-carboxamide; N-[5-(3-fluorophenyl)-2-pyrimidinyl]-3-oxospiro-[isobenzofuran-1(3H), [4'-piperidine]-1'-carboxamide; trans-3'-oxo-N-(5-phenyl-2-pyrimidinyl)]spiro[cyclohexane-1,1'(3'H)-isobenzofuran]-4-carboxamide; trans-3'-oxo-N-[1-(3-quinolyl)-4-imidazolyl]spiro[cyclohexane-1,1'(3'H)-isobenzofuran]-4-carboxamide; trans-3-oxo-N-(5-phenyl-2-pyrazinyl)spiro[4-azaiso-benzofuran-1(3H),1'-cyclohexane]-4'-carboxamide; trans-N-[5-(3-fluorophenyl)-2-pyrimidinyl]-3-oxospiro[5-azaisobenzofuran-1(3H),1'-cyclohexane]-4'-carboxamide; trans-N-[5-(2-fluorophenyl)-2-pyrimidinyl]-3-oxospiro[5-azaisobenzofuran-1(3H),1'-cyclohexane]-4'-carboxamide; trans-N-[1-(3,5-difluorophenyl)-4-imidazolyl]-3-oxospiro[7-azaisobenzofuran-1(3H),1'-cyclohexane]-4'-carboxamide; trans-3-oxo-N-(1-phenyl-4-pyrazolyl)spiro[4-azaisobenzofuran-1(3H),1'-cyclohexane]-4'-carboxamide; trans-N-[1-(2-fluorophenyl)-3-pyrazolyl]-3-oxospiro[6-azaisobenzofuran-1 (3H),1'-cyclohexane]-4'-carboxamide; trans-3-oxo-N-(I-phenyl-3-pyrazolyl)spiro[6-azaisobenzofuran-1(3H),1'-cyclohexane]-4'-carboxamide; and trans-3-oxo-N-(2-phenyl-1,2,3-triazol-4-yl)spiro[6-azaisobenzofuran-1(3H),1'-cyclohexane]-4'-carboxamide, all of which can be prepared as described in described in PCT Publication No. WO 03/082190; and pharmaceutically acceptable salts and esters thereof.

All of the above recited U.S. patents and publications are incorporated herein by reference.

Embodiments of the present invention are illustrated by the following Examples. It is to be understood, however, that the embodiments of the invention are not limited to the specific details of these Examples, as other variations thereof will be known, or apparent in light of the instant disclosure, to one of ordinary skill in the art.

EXAMPLES

Unless specified otherwise, starting materials are generally available from commercial sources such as Aldrich Chemicals Co. (Milwaukee, Wis.), Lancaster Synthesis, Inc. (Windham, N.H.), Acros Organics (Fairlawn, N.J.), Maybridge Chemical Company, Ltd. (Cornwall, England), Tyger Scientific (Princeton, N.J.), and AstraZeneca Pharmaceuticals (London, England).

General Experimental Procedures

NMR spectra were recorded on a Varian Unity™ 400 (available from Varian Inc., Palo Alto, Calif.) at room temperature at 400 MHz for proton. Chemical shifts are expressed in parts per million (δ) relative to residual solvent as an internal reference. The peak shapes are denoted as follows: s, singlet; d, doublet; t, triplet; q, quartet; m, multiplet; bs, broad singlet; 2s, two singlets. Atmospheric pressure chemical ionization mass spectra (APCI) were obtained on a Fisons™Platform II Spectrometer (carrier gas: acetonitrile: available from Micromass Ltd, Manchester, UK). Chemical ionization mass spectra (Cl) were obtained on a Hewleft-Packard™ 5989 instrument (ammonia ionization, PBMS: available from Hewlett-Packard Company, Palo Alto, Calif.). Electrospray ionization mass spectra (ES) were obtained on a Waters™ ZMD instrument (carrier gas: acetonitrile: available from Waters Corp., Milford, Mass.). Where the intensity of chlorine or bromine-containing ions are described, the expected intensity ratio was observed (approximately 3:1 for $^{35}Cl/^{37}Cl$-containing ions and 1:1 for $^{79}Br/^{81}Br$-containing ions) and the intensity of only the lower mass ion is given. In some cases only representative $^1H$ NMR peaks are given. MS peaks are reported for all examples. Optical rotations were determined on a PerkinElmer™ 241 polarimeter (available from PerkinElmer Inc., Wellesley, Mass.) using the sodium D line (λ=589 nm) at the indicated temperature and are reported as follows $[\alpha]_D^{temp}$, concentration (c=g/100 ml), and solvent.

Column chromatography was performed with either Baker™ silica gel (40 μm; J. T. Baker, Phillipsburg, N.J.) or Silica Gel 50 (EM Sciences™, Gibbstown, N.J.) in glass columns or in Flash 40 Biotage™ columns (ISC, Inc., Shelton, Conn.) under low nitrogen pressure.

Preparation of Key Intermediates

Preparation of Intermediate
7-Hydroxy-2,2-dimethyl-benzo[1,3]dioxin-4-one
(I-1a)

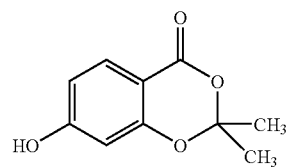

(I-1a)

A suspension of 2,4-dihydroxybenzoic acid (85.0 g) in trifluoroacetic acid (800 mL) was cooled in an ice/water bath as trifluoroacetic anhydride (500 mL) followed by the addition of acetone (100 mL). After the addition was complete, the ice/water bath was removed and the reaction mixture stirred for 24 hours before the volatiles were removed under vacuum using a rotary evaporator. The residue was cautiously added to a water/sodium bicarbonate suspension to afford a neutralized mixture. The mixture was extracted with ethyl acetate and the combined organic phases were washed with brine, dried over magnesium sulfate, filtered and evaporated. The residue was triturated with dichloromethane to afford the product (I-1a) as an off-white solid.

$^1$H NMR (CDCl$_3$): δ 1.71 (s, 6H), 6.41 (d, 1H, J=2.5 Hz), 6.59 (dd, 1H, J=8.7, 2.5 Hz), 7.82 (d, 1H, J=8.2 Hz).

Preparation of Intermediate 4-(2,2-Dimethyl-4-oxo-4H-benzo[1,3]dioxin-7-yloxy)-3-fluoro-benzaldehyde (I-1b-1)

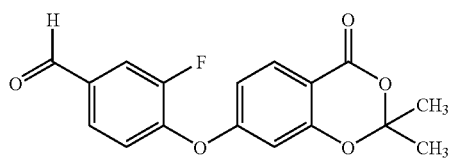

(I-1b-1)

7-Hydroxy-2,2-dimethyl-benzo[1,3]dioxin-4-one (I-1a: 12.9 g), 3,4-difluorobenzaldehyde (9.45 g) and potassium carbonate (27.6 g) were combined in dimethylformamide (100 mL) and stirred as the reaction mixture was heated to 80° C. After 24 hours, the reaction mixture was cooled to ambient temperature, combined with water, and extracted with ethyl acetate. The combined organic phases were dried over magnesium sulfate, filtered, and evaporated. The residue was purified by column chromatography on silica gel eluting with 10-15% ethyl acetate in heptane to give the title compound (I-1b-1).

$^1$H NMR (CDCl$_3$): δ 1.71 (s, 6H), 6.49 (d, 1H, J=2.5 Hz), 6.73 (dd, 1H, J=8.7, 2.5 Hz), 7.28 (t, 1H, J=7.5Hz), 7.70-7.75 (m, 2H), 7.94 (d, 1H, J=8.7Hz), 9.96 (d, 1H, J=1.6Hz).

Preparation of Intermediate 4-(2,2-Dimethyl-4-oxo-4H-benzo[1,3]dioxin-7-yloxy)-3,5-difluoro-benzaldehyde (I-1b-2)

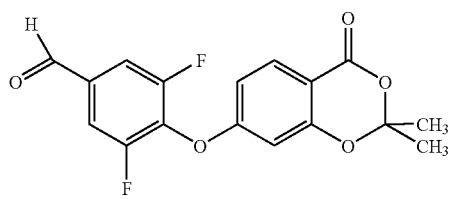

(I-1b-2)

7-Hydroxy-2,2-dimethyl-benzo[1,3]dioxin-4-one (I-1a: 12.9 g) and 3,4,5-trifluorobenzaldehyde (5.0 g) and potassium carbonate (27.6 g) were combined in dimethylformamide (100 mL) and stirred as the reaction mixture was heated to 80° C. After 24 hours, the reaction mixture was cooled to ambient temperature, combined with water, and extracted with ethyl acetate. The combined organic phases were dried over magnesium sulfate, filtered, and evaporated. The residue was purified by column chromatography on silica gel eluting with 5-10% ethyl acetate in heptane to give the title compound (I-1b-2).

$^1$H NMR (CDCl$_3$): δ 1.71 (s, 6H), 6.45 (d, 1H, J=2.5 Hz), 6.70 (dd, 1H, J=8.7, 2.5 Hz), 7.56-7.61 (m, 2H), 7.93 (d, 1H, J=8.7 Hz), 9.93 (t, 1H, J=1.6 Hz).

Preparation of Intermediate 7-{2-Fluoro-4-[(3-methyl-butylamino)-methyl]-phenoxy}-2,2-dimethyl-benzo[1,3]dioxin-4-one (I-1c-1)

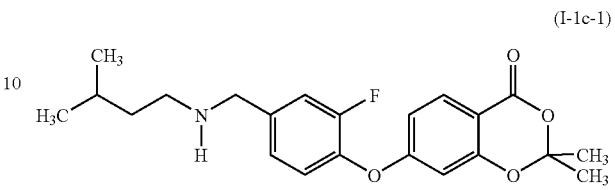

(I-1c-1)

4-(2,2-Dimethyl-4-oxo-4H-benzo[1,3]dioxin-7-yloxy)-3-fluoro-benzaldehyde (I-1b-1: 30.0 g) and 3-methyl-butylamine (9.15 g) were combined in 1,2-dichloroethane (1.0 L). After stirring at ambient temperature for 1 hour, sodium triacetoxyborohydride (100 g) was added to the solution. After stirring overnight, the reaction mixture was treated with an aqueous 2 N potassium hydroxide solution, the organic phase was separated, dried over magnesium sulfate, filtered, and evaporated to provide the title compound (I-1c-1).

$^1$H NMR (CDCl$_3$): δ 0.89 (d, 6H, J=6.2 Hz), 1.40-1.50 (m, 2H), 1.6-1.7 (m, 1H), 1.70 (s, 6H), 2.66 (m, 2H), 3.79 (s, 2H), 6.39 (d, 1H, J=2.5 Hz), 6.67 (dd, 1H, J=8.7, 2.5 Hz), 7.10-7.25 (m, 3H), 7.88 (d, 1H, J=8.7 Hz).

Preparation of Intermediate 7-{4-[(2-Cyclopropyl-ethylamino)-methyl]-2-fluoro-phenoxy}-2,2-dimethyl-benzo[1,3]dioxin-4-one (I-1c-2)

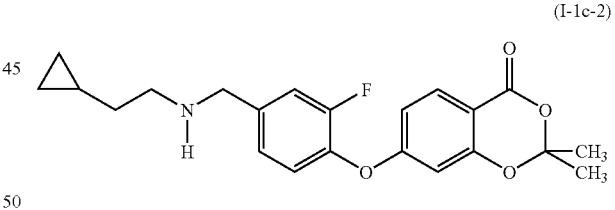

(I-1c-2)

4-(2,2-Dimethyl-4-oxo-4H-benzo[1,3]dioxin-7-yloxy)-3-fluoro-benzaldehyde (I-1b-1: 24.8 g) and 2-cyclopropyl-ethylamine (6.2 g) were combined in 1,2-dichloroethane (1.0 L). After stirring at ambient temperature for 1 hour, sodium triacetoxyborohydride (83 g) was added to the solution. After stirring overnight, the reaction mixture was treated with an aqueous 2 N potassium hydroxide solution, the organic phase was separated, dried over magnesium sulfate, filtered, and evaporated to provide the title compound (I-1c-2).

$^1$H NMR (CDCl$_3$): δ 0.0-0.1 (m, 2H), 0.4-0.45 (m, 2H), 0.6-0.7 (m, 1H), 1.4-1.5 (m, 2H), 1.69 (s, 6H), 2.72 (t, 2H, J=7.0), 3.79 (s, 2H), 6.38 (d, 1H, J=2.5 Hz), 6.66 (dd, 1H, J=8.7, 2.5 Hz), 7.1-7.3 (m, 3H), 7.87 (d, 1H, J=8.7 Hz).

Preparation of Intermediate 7-{2,6-Difluoro-4-[(3-methyl-butylamino)-methyl]-phenoxy}-2,2-dimethyl-benzo[1,3]dioxin-4-one (I-1c-3)

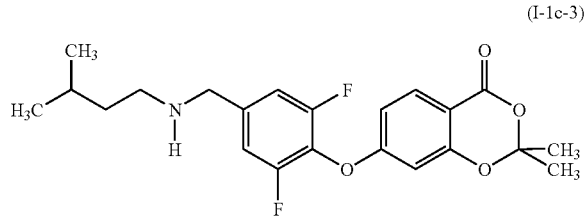

(I-1c-3)

4-(2,2-Dimethyl-4-oxo-4H-benzo[1,3]dioxin-7-yloxy)-3,5-difluoro-benzaldehyde (I-1b-2: 1.0 g) and 3-methyl-butylamine (0.31 g) were combined in 1,2-dichloroethane (25 mL). After stirring at ambient temperature for 1 hour, sodium triacetoxyborohydride (3.3 g) was added to the solution. After stirring overnight, the reaction mixture was treated with an aqueous 2 N potassium hydroxide solution, the organic phase was separated, dried over magnesium sulfate, filtered, and evaporated to provide the title compound (I-1c-3).

$^1$H NMR (CDCl$_3$): δ 0.88 (d, 6H, J=6.6 Hz), 1.35-1.45 (m, 2H), 1.60-1.70 (m, 1H), 1.69 (s, 6H), 2.62 (m, 2H), 3.77 (s, 2H), 6.41 (d, 1H, J=2.5 Hz), 6.68 (dd, 1H, J=8.7, 2.5 Hz), 7.03 (d, 2H, J=8.7 Hz), 7.89 (d, 1H, J=8.7 Hz).

Preparation of Intermediate [4-(2,2-Dimethyl-4-oxo-4H-benzo[1,3]dioxin-7-yloxy)-3-fluoro-benzyl]-(3-methyl-butyl)-carbamic acid tert-butyl ester (I-1d-1)

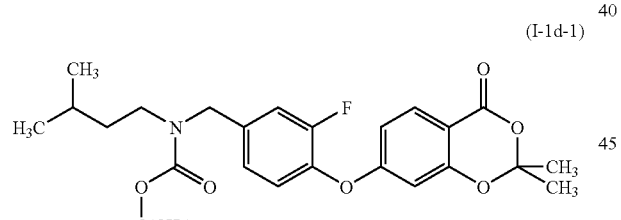

(I-1d-1)

7-{2-Fluoro-4-[(3-methyl-butylamino)-methyl]-phenoxy}-2,2-dimethyl-benzo[1,3]dioxin-4-one (I-1c-1: 40 g), Boc$_2$O (34 g) and potassium carbonate (20 g) were combined in ethyl acetate (400 mL) and the mixture heated to 50° C. After 6 hours, water was added to the reaction mixture and the organic layer was separated, dried over magnesium sulfate, filtered, and concentrated. The residue was purified by chromatography on silica gel eluting with ethyl acetate in heptane to afford the title compound (I-1d-1).

$^1$H NMR (CDCl$_3$): δ 0.80-0.90 (m, 6H), 1.69 (s, 6H), 6.38 (d, 1H, J=2.5 Hz), 6.66 (dd, 1H, J=8.7, 2.5 Hz), 7.00-7.15 (m, 3H), 7.88 (d, 1H, J=8.7 Hz).

Preparation of Intermediate (2-Cyclopropyl-ethyl)-[4-(2,2-dimethyl-4-oxo-4H-benzo[1,3]dioxin-7-yloxy)-3-fluoro-benzyl]-carbamic acid tert-butyl ester (I-1d-2)

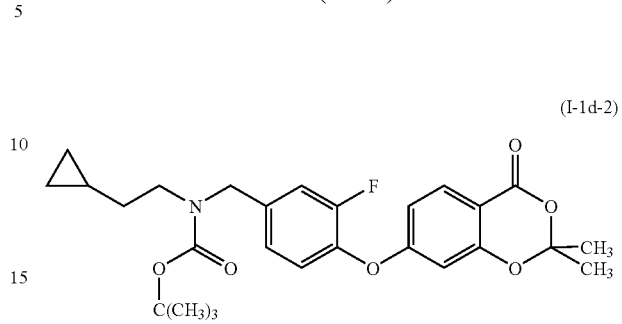

(I-1d-2)

7-{4-[(2-Cyclopropyl-ethylamino)-methyl]-2-fluoro-phenoxy}-2,2-dimethyl-benzo[1,3]dioxin-4-one (I-1c-2: 30 g), Boc$_2$O (25 g) and potassium carbonate (20 g) were combined in ethyl acetate (300 mL) and the mixture heated to 50° C. After 6 hours, water was added to the reaction mixture and the organic layer was separated, dried over magnesium sulfate, filtered, and concentrated. The residue was purified by chromatography on silica gel eluting with ethyl acetate in heptane to afford the title compound (I-1d-2).

$^1$H NMR (CDCl$_3$): δ 0.0-0.1 (m, 2H), 0.4-0.45 (m, 2H), 0.5-0.7 (m, 1H), 1.4-1.5 (m, 2H), 1.69 9s, 9H), 1.71 (s, 6H), 3.2-3.4 (m, 2H), 4.3-4.5 (m, 2H), 6.39 (d, 1H, J=2.5 Hz), 6.66 (dd, 1H, J=8.7, 2.5 Hz), 7.00-7.25 (m, 3H), 7.87 (d, 1H, J=8.7 Hz).

Preparation of Intermediate [4-(2,2-Dimethyl-4-oxo-4H-benzo[1,3]dioxin-7-yloxy)-3,5-difluoro-benzyl]-(3-methyl-butyl)-carbamic acid tert-butyl ester (I-1d-3)

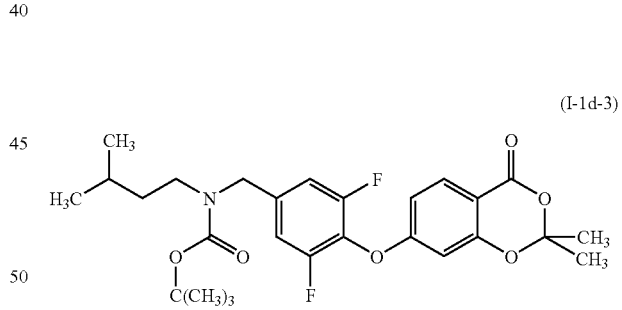

(I-1d-3)

7-{2,6-Difluoro-4-[(3-methyl-butylamino)-methyl]-phenoxy}-2,2-dimethyl-benzo[1,3]dioxin-4-one (I-1c-3: 1.2 g), Boc$_2$O (1.5 g) and potassium carbonate (1.2 g) were combined in ethyl acetate (20 mL) and the mixture heated to 50 C. After 6 hours, water was added to the reaction mixture and the organic layer was separated, dried over magnesium sulfate, filtered, and concentrated. The residue was purified by chromatography on silica gel eluting with ethyl acetate in heptane to afford the title compound (I-1d-3).

$^1$H NMR (CDCl$_3$): δ 0.89 (d, 6H, J=6.6 Hz), 1.35-1.59 (m, 3H), 1.70 (s, 6H), 3.15-3.30 (m, 2H), 4.30-4.45 (m, 2H), 6.41 (d, 1H, J=2.5 Hz), 6.68 (dd, 1H, J=8.7, 2.5 Hz), 6.90 (d, 2H, J=8.3 Hz), 7.89 (d, 1H, J=8.7 Hz).

Preparation of Intermediate [4-(4-Carbamoyl-3-hydroxy-phenoxy)-3-fluoro-benzyl]-(3-methyl-butyl)-carbamic acid tert-butyl ester (I-1e-1)

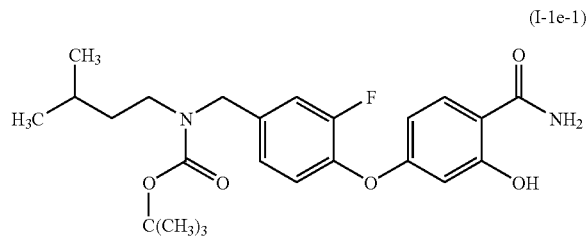

[4-(2,2-Dimethyl-4-oxo-4H-benzo[1,3]dioxin-7-yloxy)-3-fluoro-benzyl]-(3-methyl-butyl)-carbamic acid tert-butyl ester (I-1d-1: 20 g) was dissolved in 35 mL of a 2 M solution of ammonia in isopropanol. The resulting solution was then treated with 50 mL of a saturated aqueous ammonia solution and the resulting mixture heated at 80° C. After 8 hours, the reaction mixture was cooled to ambient temperature and concentrated with a rotary evaporator. The residue was diluted with ethyl acetate and the organic solution was washed twice with water, once with brine, dried over magnesium sulfate, filtered, and concentrated. The residue was purified by column chromatography on silica gel eluting with 50% ethyl acetate in heptane to afford the title compound (I-1e-1).

$^1$H NMR (CDCl$_3$): δ 0.88 (d, 6H, J=6.2 Hz), 1.35-1.60 (m, 12H), 3.10-3.35 (m, 2H), 4.35-4.50 (m, 2H), 6.40 (s, 1H), 6.48 (d, 1H, J=7.5 Hz), 6.95-7.20 (m, 3H), 7.32 (d, 1H, J=8.7 Hz), 12.45 (s, 1H).

Preparation of Intermediate [4-(4-Carbamoyl-3-hydroxy-phenoxy)-3-fluoro-benzyl]-(2-cyclopropyl-ethyl)-carbamic acid tert-butyl ester (I-1e-2)

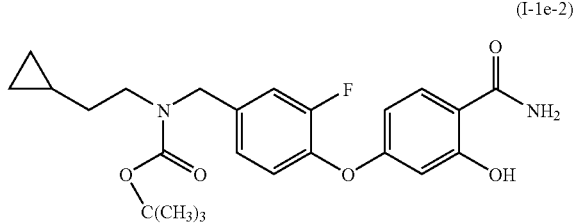

(2-Cyclopropyl-ethyl)-[4-(2,2-dimethyl-4-oxo-4H-benzo[1,3]dioxin-7-yloxy)-3-fluoro-benzyl]-carbamic acid tert-butyl ester (I-1d-2: 15.8 g) was dissolved in 35 mL of a 2 M solution of ammonia in isopropanol. The resulting solution was then treated with 50 mL of a saturated aqueous ammonia solution and the resulting mixture heated at 80° C. After 8 hours, the reaction mixture was cooled to ambient temperature and concentrated with a rotary evaporator. The residue was diluted with ethyl acetate and the organic solution was washed twice with water, once with brine, dried over magnesium sulfate, filtered, and concentrated. The residue was purified by column chromatography on silica gel eluting with 50% ethyl acetate in heptane to afford the title compound (I-1e-2).

$^1$H NMR (CDCl$_3$): δ 0.0-0.1 (m, 2H), 0.40-0.45 (m, 2H), 0.50-0.70 (m, 1H), 1.4-1.5 (m, 2H), 1.49 (s, 9H), 3.2-3.4 (m, 2H), 4.35-4.50 (m, 2H), 6.40 (s, 1H), 6.49 (m, 1H), 6.85-6.95 (m, 2H), 7.33 (d, 1H, J=8.7 Hz).

Preparation of Intermediate [4-(4-Carbamoyl-3-hydroxy-phenoxy)-3,5-difluoro-benzyl]-(3-methyl-butyl)-carbamic acid tert-butyl ester (I-1e-3)

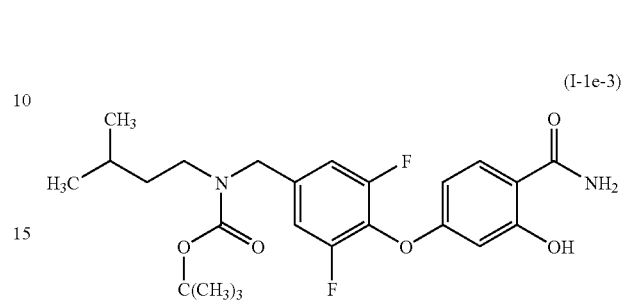

[4-(2,2-Dimethyl-4-oxo-4H-benzo[1,3]dioxin-7-yloxy)-3,5-difluoro-benzyl]-(3-methyl-butyl)-carbamic acid tert-butyl ester (I-1d-3: 1.0 g) was dissolved in 2.0 mL of a 2 M solution of ammonia in isopropanol. The resulting solution was then treated with 1.5 mL of a saturated aqueous ammonia solution and the resulting mixture heated at 80° C. After 8 hours, the reaction mixture was cooled to ambient temperature and concentrated with a rotary evaporator. The residue was diluted with ethyl acetate and the organic solution was washed twice with water, once with brine, dried over magnesium sulfate, filtered, and concentrated. The residue was purified by column chromatography on silica gel eluting with 50% ethyl acetate in heptane to afford the title compound (I-1e-3).

$^1$H NMR (CDCl$_3$): δ 0.89 (d, 6H, J=6.6 Hz), 1.35-1.59 (m, 3H), 3.15-3.30 (m, 2H), 4.30-4.45 (m, 2H), 6.39 (s, 1H), 6.52 (d, 1H, J=7.1 Hz), 6.88 (d, 2H, J=8.3 Hz), 7.32 (d, 1H, J=8.7 Hz), 12.45 (s, 1H).

Example 1

Preparation of 4-(2-fluoro-4-{[(3-methylbutyl)amino]methyl}phenoxy)-2-hydroxybenzamide, hydrochloride salt (1A)

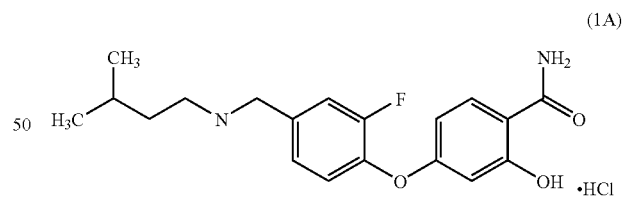

[4-(4-Carbamoyl-3-hydroxy-phenoxy)-3-fluoro-benzyl]-(3-methyl-butyl)-carbamic acid tert-butyl ester (I-1e-1: 15 g) was dissolved in 150 mL of dichloromethane and treated with 50 mL of a 4.0 M hydrogen chloride solution in dioxane. After stirring 24 hours at room temperature, the volatiles were removed under reduced pressure and the resulting crude material was suspended in methanol, heated at reflux for 20 minutes, and stirred overnight at room temperature. The resulting slurry was collect via filtration, rinsed with chilled methanol, and dried under vacuum to provide the title compound (1A).

$^1$H NMR (CD$_3$OD): δ 0.97 (d, 6H, J=6.2 Hz), 1.55-1.75 (m, 3H), 3.05-3.15 (m, 2H), 4.22 (s, 2H), 6.31 (d, 1H, J=2.5 Hz), 6.48 (dd, 1H, J=8.7, 2.5 Hz), 7.29 (t, 1H, J=7.5 Hz), 7.36 (dd, 1H, J=8.5, 1.6 Hz), 7.47 (dd, 1H, J=11.2, 2.1 Hz), 7.75 (d, 1H, J=9.1 Hz). MS: 347 (M+1)

Example 2

Comparator

Preparation of Comparator compound 3-(2-fluoro-4-{[(3-methylbutyl)amino]-methyl}phenoxy)phenol, hydrochloride salt (2A)

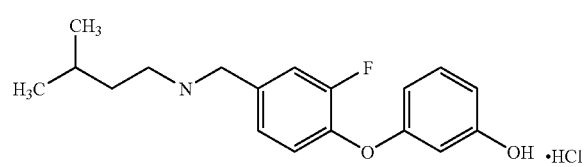

(2A-Comparator)

Cesium carbonate (2.757 g, 8.44 mmol) was added to a solution of 3,4-difluoro-benzaldehyde (1.0 g, 7.037 mmol) and 3-methoxyphenol (875 mg, 7.05 mmol) dissolved in DMF (20 mL). The reaction was heated to 120° C. for 24 hours. The reaction mixture was then poured into 300 mL of water and extracted 3 times with 60 mL of ethyl acetate. The combined organic layers were washed with water (2 times), brine, and dried over sodium sulfate. The organic layer was filtered and concentrated under reduced pressure. 3-Fluoro-4-(3-methoxy-phenoxy)-benzaldehyde (1.0 g) was isolated using flash silica gel and eluting with 10% ethyl acetate and heptane.

The (3-fluoro-4-(3-methoxy-phenoxy)-benzaldehyde, 0.50 g, 2.03 mmol) was dissolved in methanol (10 mL) and to which was added isoamyl amine (0.267 g, 3.05 mmol). The reaction was allowed to stir overnight at room temperature. Sodium borohydride (0.235 g, 6.1 mmol) was added and the reaction was stirred for 1 hour at room temperature. The reaction mixture was treated with concentrated (37%) hydrochloric acid, the volatiles were removed under reduced pressure, 2 N aqueous sodium hydroxide added to make basic and the resulting mixture extracted with ethyl acetate (2 times). The combined organics were washed with saturated aqueous sodium bicarbonate and dried over sodium sulfate, filtered, and concentrated under reduced pressure to [3-Fluoro-4-(3-methoxy-phenoxy)-benzyl]-(3-methyl-butyl)-amine.

The [3-fluoro-4-(3-methoxy-phenoxy)-benzyl]-(3-methyl-butyl)-amine (460 mg, 1.45 mmol) was dissolved in dichloromethane (10 ml) and cooled to −78° C. as boron tribromide (7.25 mL of a 1.0 M in dichloromethane, 7.25 mmol) was added slowly. After 1 hour at −78° C., the reaction was allowed to warm to room temperature. After 4 hours at room temperature the reaction mixture was carefully being quenched with cold water before the pH was adjusted to 10.0 using concentrated ammonium hydroxide. The reaction mixture was extracted with dichloromethane two times and the combined organic layers were washed with brine, dried over sodium sulfate, filtered, and concentrated. The residue was purified by preparative thin layer chromatography on silica eluting with 5% methanol in ethyl acetate. The HCl salt of the product thus isolated was formed by dissolving the free base in ethyl acetate and adding 1 ml of 4.0 M HCl in dioxane and evaporating to afford the product (2A) a solid.

¹H NMR (CD₃OD): δ 0.97 (d, 6H, J=6.6 Hz), 1.55-1.75 (m, 3H), 3.04-3.09 (m, 2H), 4.18 (s, 2H), 6.36-6.41 (m, 2H), 6.54-6.57 (m, 1H), 7.09-7.15 (m, 2H), 7.26 (d, 1H, J=8.3 Hz), 7.40 (dd, 1H, 11.2, 2.0 Hz). MS: 304 (M+1)

Example 3

Preparation of 4-(4-{[(2-cyclopropylethyl)amino]methyl}-2-fluorophenoxy)-2-hydroxybenzamide, hydrochloride salt (3A)

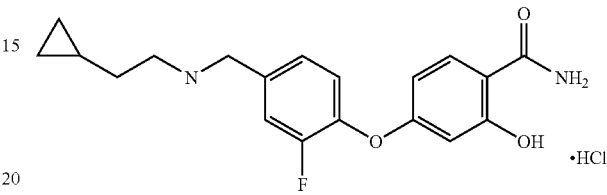

(3A)

[4-(4-Carbamoyl-3-hydroxy-phenoxy)-3-fluoro-benzyl]-(2-cyclopropyl-ethyl)-carbamic acid tert-butyl ester (I-1e-2: 9.92 g) was dissolved in 150 mL of dichloromethane and treated with 40 mL of a 4.0 M hydrogen chloride solution in dioxane. After stirring 24 hours at room temperature, the volatiles were removed under reduced pressure and the resulting crude material was suspended in methanol, heated at reflux for 20 minutes and stirred overnight at room temperature. The resulting slurry was collect via filtration, rinsed with chilled methanol, and dried under vacuum to provide the title compound (A).

¹H NMR (CD₃OD): δ 0.14-0.18 (m, 2H), 0.50-0.60 (m, 2H), 0.70-0.80 (m, 1H), 1.61 (m, 2H), 3.10-3.20 (m, 2H), 4.23 (s, 2H), 6.31 (d, 1H, J=2.5 Hz), 6.48 (dd, 1H, J=9.1, 2.5 Hz), 7.29 (t, 1H, J=8.1 Hz), 7.36 (dd, 1H, J=1.6, 8.3 Hz), 7.47 (dd, 1H, 2.1, 10.8 Hz), 7.75 (d, 1H, J=9.9 Hz). MS: 345 (M+1)

The compounds listed in Table 1 below were prepared using procedures analogous to those described above for the synthesis of Examples 1A and 3A above using the appropriate starting materials which are available commercially, prepared using preparations well-known to those skilled in the art, or prepared in a manner analogous to routes described above for other intermediates. Unless indicated otherwise, the compounds listed in the table below were isolated and tested as their hydrochloride salt. The salts can be easily converted to their corresponding free base by treating with base.

TABLE 1

| Example No. | $R^1$ | $R^2$ | $R^3$ | $R^4$ | $R^5$ | $R^6$ |
|---|---|---|---|---|---|---|
| 3B | H | (indanyl) | H | H | F | H |

¹H NMR (CD₃OD): δ 3.20 (dd, 2H, J = 6.7, 16.6 Hz), 3.47 (dd, 2H, J = 8.3, 16.6 Hz), 4.17 (m, 1H), 4.34 (s, 2H), 6.33 (d, 1H,

TABLE 1-continued

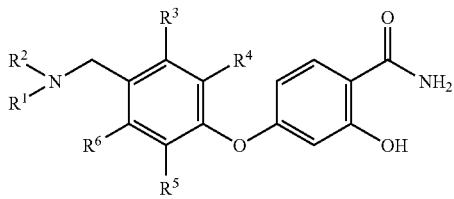

| Example No. | R¹ | R² | R³ | R⁴ | R⁵ | R⁶ |
|---|---|---|---|---|---|---|

J = 2.5 Hz), 6.48 (dd, 1H, J = 2.5, 8.7 Hz), 7.2-7.3 (m, 5H), 7.4 (d, 1H), 7.55 (d, 1H), 7.75 (d, 1H).

MS: 393 (M + 1)

| 3C* | H | (CH₃)₂CH—O—(CH₂)₂— | H | H | F | H |

¹H NMR (CDCl₃): δ 1.16 (d, 6H, J = 6.2 Hz), 2.78 (m, 2H), 3.55 (m, 3H), 3.80 (s, 2H), 6.39 (d, 1H, J = 2.5 Hz), 6.49 (dd, 1H, J = 8.7, 2.5 Hz), 7.1-7.35 (m, 4H).
MS: 363 (M + 1)

| 3D* | H | 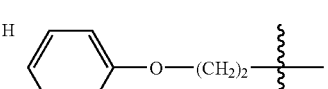 | H | H | F | H |

¹H NMR (CDCl₃): δ 3.03 (m, 2H), 3.87 (s, 2H), 4.10 (m, 2H).
MS: 397 (M + 1)

| 3E | H | 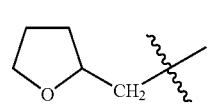 | H | H | F | H |

¹H NMR (CD₃OD): δ 1.6-1.7 (m, 1H), 1.9-2.0 (m, 2H), 2.1-2.2 (m, 1H), 2.95-3.05 (m, 1H), 3.15-3.25 (m, 1H), 3.8-3.9 (m, 1H), 3.9-4.0 (m, 1H), 4.15-4.25 (m, 1H), 4.25-4.30 (m, 2H).
MS: 361 (M + 1)

| 3F | H | 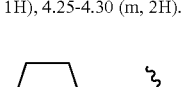 | H | H | F | H |

¹H NMR (CD₃OD): δ 1.6-1.7 (m, 1H), 1.9-2.0 (m, 2H), 2.1-2.2 (m, 1H), 2.95-3.05 (m, 1H), 3.15-3.25 (m, 1H), 3.8-3.9 (m, 1H), 3.9-4.0 (m, 1H), 4.15-4.25 (m, 1H), 4.25-4.30 (m, 2H).
MS: 361 (M + 1)

| 3G | H | 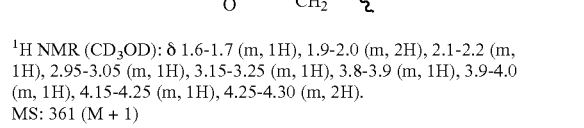 | H | H | F | H |

¹H NMR (CD₃OD): δ 1.6-1.7 (m, 1H), 1.9-2.0 (m, 2H), 2.1-2.2 (m, 1H), 2.95-3.05 (m, 1H), 3.15-3.25 (m, 1H), 3.8-3.9 (m, 1H), 3.9-4.0 (m, 1H), 4.15-4.25 (m, 1H).

MS: 361 (M + 1)

| 3H | H | 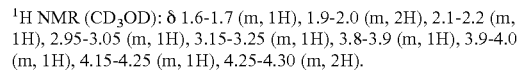 | H | H | F | H |

¹H NMR (CD₃OD): δ 1.3-1.4 (m, 2H), 1.65-1.75 (m, 2H), 2.0-2.1 (m, 1H), 2.99 (d, 1H, J = 7.0 Hz), 3.4-3.5 (m, 2H), 3.9-4.0 (m, 2H), 4.25 (s, 2H).
MS: 375 (M + 1)

| 3I | H | 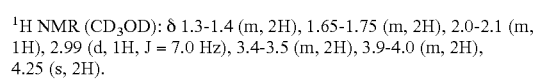 | H | H | F | H |

TABLE 1-continued

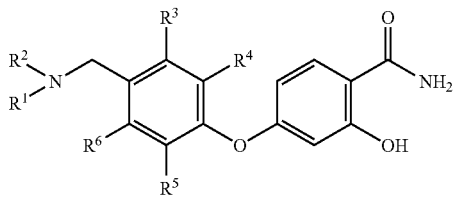

| Example No. | R¹ | R² | R³ | R⁴ | R⁵ | R⁶ |
|---|---|---|---|---|---|---|

¹H NMR (CD₃OD): δ 1.30-1.75 (m, 10H), 2.94 (s, 2H), 4.26 (s, 2H), 6.33 (d, 1H, J = 2.5 Hz), 6.48 (dd, 1H, J = 8.7, 2.5 Hz), 7.30 (t, 1H, J = 7.9 Hz), 7.4 (d, 1H), 7.75 (d, 1H, J = 9.1 Hz).
MS: 389 (M + 1)

| 3J* | H | 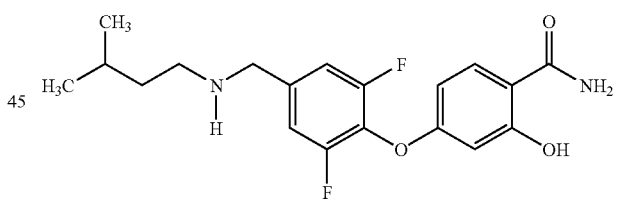 | H | H | F | H |

¹H NMR (CD₃OD): δ 0.79 (t, 3H, J = 7.5 Hz), 1.7-1.9 (m, 2H), 3.59 (s, 2H), 3.67-3.68 (m, 1H), 6.25 (d, 1H, J = 2.5 Hz), 6.38 (dd, 1H, J = 8.7, 2.5 Hz), 7.05-7.15 (m, 2H), 7.20 (d, 1H), 7.25-7.35 (m, 1H), 7.46 (d, 1H, J = 7.9 Hz), 7.71 (d, 1H, J = 8.7 Hz), 7.80-7.85 (m, 1H), 8.50 (d, 1H).
MS: 396 (M + 1)

*Isolated as the free base

Example 4

Preparation of 4-(2,6-difluoro-4-{[(3-methybutyl)amino]methyl}phenoxy)-2-hydroxybenzamide (4A)

(4A)

[4-(4-Carbamoyl-3-hydroxy-phenoxy)-3,5-difluoro-benzyl]-(3-methyl-butyl)-carbamic acid tert-butyl ester (I-1e-3: 0.8 g) was dissolved in 5 mL of dichloromethane and treated with 2.5 ml of a 4.0 M hydrogen chloride solution in dioxane. After stirring 24 hours at room temperature, the volatiles were removed under reduced pressure and the resulting crude material was suspended in methanol, heated at reflux for 20 minutes, and stirred overnight at room temperature. The resulting slurry was collect via filtration, rinsing with chilled methanol, and dried under vacuum to provide the title compound (4A).

¹H NMR (CD₃OD): δ 0.97 (d, 6H, J=6.6 Hz), 1.55-1.75 (m, 3H), 3.05-3.15 (m, 2H), 4.24 (s, 2H), 6.29 (d, 1H, J=2.5 Hz), 6.49 (dd, 1H, J=8.7, 2.5 Hz), 7.35 (d, 2H, J=8.3 Hz), 7.75 (d, 1H, J=8.7 Hz). MS: 365 (M+1)

The compounds listed in Table 2 below were prepared using procedures analogous to those described above for the synthesis of Examples 4A above using the appropriate starting materials which are available commercially, prepared using preparations well-known to those skilled in the art, or prepared in a manner analogous to routes described above for other intermediates. All the compounds listed in the table below were isolated as their hydrochloride salts.

TABLE 2

| Example No. | R¹ | R² | R³ | R⁴ | R⁵ | R⁶ |
|---|---|---|---|---|---|---|
| 4B | H | cyclohexyl-CH< | H | F | F | H |

¹H NMR (CD₃OD): δ 1.20-1.30 (m, 1H), 1.35-1.45 (m, 4H), 1.70-1.80 (m, 1H), 1.85-1.95 (m, 2H), 2.15-2.05 (m, 2H), 3.10-3.20 (m, 1H), 4.26 (s, 2H), 6.28 (d, 1H, J = 2.5 Hz), 6.49 (dd, 1H, J = 8.7, 2.5 Hz), 7.36 (d, 2H, J = 8.3 Hz), 7.75 (d, 1H, J = 9.1 Hz).
MS: 377 (M + 1)

| 4C | H | cyclopropyl-(CH₂)₂- | H | F | F | H |

¹H NMR (CD₃OD): δ 0.14-0.18 (m, 2H), 0.50-0.60 (m, 2H), 0.70-0.80 (m, 1H), 1.60-1.70 (m, 2H), 3.10-3.20 (m, 2H), 4.24 (s, 2H), 6.29 (d, 1H, J = 2.5 Hz), 6.49 (dd, 1H, J = 8.7, 2.5 Hz), 7.35 (d, 2H, J = 8.3 Hz), 7.75 (d, 1H, J = 9.1 Hz).
MS: 363 (M + 1)

| 4D | H | tetrahydrofuran-2-yl-CH₂- | H | F | F | H |

¹H NMR (CD₃OD): δ 1.55-1.70 (m, 1H), 1.90-2.00 (m, 2H), 2.10-2.20 (m, 1H), 2.95-3.05 (m, 1H), 3.20-3.25 (m, 1H), 3.75-3.85 (m, 1H), 3.90-3.95 (m, 1H), 4.15-4.25 (m, 1H), 4.25-4.30 (m, 2H). 6.33 (d, 1H, J = 2.5 Hz), 6.49 (dd, 1H, J = 8.7, 2.5 Hz), 7.38 (d, 2H, J = 8.3 Hz), 7.76 (d, 1H, J = 9.1 Hz).
MS: 379 (M + 1)

| 4E | H | tetrahydropyran-4-yl-(CH₂)₂- | H | F | F | H |

¹H NMR (CD₃OD): δ 1.25-1.40 (m, 3H), 1.60-1.75 (m, 4H), 3.10-3.20 (m, 2H), 3.35-3.45 (m, 2H), 3.90-3.95 (m, 2H), 4.25 (s, 2H), 6.33 (d, 1H, J = 2.5 Hz), 6.49 (dd, 1H, J = 8.7, 2.5 Hz), 7.38 (d, 2H, J = 7.9 Hz), 7.76 (d, 1H, J = 9.1 Hz).
MS: 407 (M + 1)

| 4F | H | indan-2-yl | H | F | F | H |

TABLE 2-continued

| Example No. | R¹ | R² | R³ | R⁴ | R⁵ | R⁶ |
|---|---|---|---|---|---|---|

¹H NMR (CD₃OD): δ 3.21 (dd, 2H, J = 6.6, 16.6 Hz), 3.48 (dd, 2H, J = 7.9, 16.6 Hz), 4.19 (m, 1H), 4.36 (s, 2H), 6.30 (d, 1H, J = 2.5 Hz), 6.49 (dd, 1H, J = 2.5, 9.1 Hz), 7.20-7.25 (m, 2H), 7.26-7.30 (m, 2H), 7.35-7.45 (m, 2H), 7.75 (d, 1H, J = 9.1 Hz).
MS: 411 (M + 1)

Pharmacological Testing

The practice of the instant invention for treating obesity or related eating disorders (including promoting weight loss or reducing weight gain) can be evidenced by activity in at least one of the protocols described hereinbelow.

In Vitro Biological Assays

Binding Assay

The test compounds where diluted in 100% DMSO ($10^{-10}$ M to $10^{-5}$ M) and then 2 µl were added to a 96 well polypropylene plate. 2 µl 10 µM of Naltrexone were added onto the plate for non-specific activity. [³H] Diprenorphine (DPN) was diluted in binding buffer (50 mM Tris-HCL (pH7.5), 5 mM MgCl₂, 1 mM EDTA followed by protease inhibitors: 100 µg/ml bacitracin, 100 µg/ml benzamidine, 5 µg/ml aprotinin, 5 µg/ml leupeptin) and 20 µl were added to the plate. Membranes prepared from cells expressing recombinant delta, kappa and mu opioid receptors were diluted with binding buffer and 178 µl were added to the plate. The plates were covered and placed on a orbital shaker at room temperature for 60 minutes. At the end of incubation, the plates were then harvested onto GF/C filter plates (Perkin Elmer, presoaked with 1% PEI) using ice-cold binding buffer. Each filter was washed three times. The filters were dried overnight. In the morning, 30 µl of scintillation cocktail were added onto the well and sealed. The plates were counted on a Wallac Trilux™ counter. Ki were determined by using Cheng and Prusoff equation within PRISM software. Kd values were obtained from Scatchard plot analysis.

The following bioassay system for determining the mu, kappa and delta binding properties and pharmacological activity of opioid ligands is described by Bass, R., et al., in "Identification and characterization of novel somatostatin antagonists" *Molecular Pharmacology*, 50, 709-715 (1996), which is incorporated herein by reference.

GTPγ[³⁵S] Binding Assays at Opioid Receptors

Membranes were prepared from cells as described (Bass et al, 1996). GTPγ[³⁵S] binding assays were performed in a 96 well FlashPlate™ format in duplicate using 100 pM GTPγ[³⁵S] and 5 µg membrane per well in assay buffer composed of 50 mM Tris HCl, pH 7.4, 5 mM MgCl₂, 1 mM EDTA, 100 mM NaCl, 30 µM GDP, 0.1% bovine serum albumin and the following protease inhibitors: 100 µg/ml bacitracin, 100 µg/ml benzamidine, 5 µg/ml aprotinin, 5 µg/ml leupeptin. The assay mix was then incubated at 30° C. with increasing concentrations of antagonist ($10^{-10}$ M to $10^{-5}$ M) for 10 minutes and challenged with the agonists BW-373U86 (1 nM), dynorphin-A (10 nM), β-endorphin (1 μM) for opioid receptors delta, kappa, and mu, respectively. The assays were performed at 30° C. for one hour. The FlashPlates were then centrifuged at 2000×g for 10 minutes. Stimulation of GTPγ [$^{35}$S] binding was then quantified using a Wallac Microbeta and Ki calculations were done using Prism™ by Graphpad. The average Ki values observed for the compounds listed in the Example section above are summarized in the Table below for each of the receptors; mu, kappa and delta. Each of the compounds listed below were tested as their hydrochloride salts unless indicated otherwise. Those Example Numbers with an asterisk (*) were tested as their free base.

GTPγ[$^{35}$S] binding Ki Values

| Example No. | Mu (nm) | Kappa (nm) | Delta (nm) |
|---|---|---|---|
| 1A | 0.335 (n = 4) | 0.652 (n = 4) | 0.64 (n = 2) |
| 2A (Comparator) | 16.7 (n = 2) | 47.1 (n = 2) | 25.4 (n = 2) |
| 3A | 0.312 (n = 5) | 0.39 (n = 5) | 0.62 (n = 4) |
| 3B | 0.00412 (n = 3) | 0.0348 (n = 1) | 0.041 (n = 1) |
| 3C* | 1.65 (n = 2) | 3.78 (n = 2) | 1.68 (n = 2) |
| 3D* | 0.92 (n = 2) | 5.35 (n = 2) | 0.687 (n = 2) |
| 3E | 1.17 (n = 2) | 0.47 (n = 2) | 3.25 (n = 2) |
| 3F | 0.855 (n = 2) | 0.235 (n = 2) | 2.23 (n = 2) |
| 3G | 3.91 (n = 2) | 1.09 (n = 2) | 10.3 (n = 2) |
| 3H | 4.9 (n = 2) | 1.56 (n = 2) | 3.02 (n = 2) |
| 3I | 0.158 (n = 1) | 0.215 (n = 1) | 3.33 (n = 1) |
| 3J* | 26.2 (n = 2) | 13.8 (n = 2) | 16.6 (n = 2) |
| 4A | 0.094 (n = 1) | 0.164 (n = 1) | 0.465 (n = 1) |
| 4B | 0.0772 (n = 1) | 0.0731 (n = 1) | 0.866 (n = 1) |
| 4C | 0.167 (n = 1) | 0.244 (n = 1) | 1.10 (n = 1) |
| 4D | 0.346 (1) | 0.184 (1) | 4.87 (1) |
| 4E | 0.0963 (n = 1) | 0.419 (n = 1) | 0.352 (n = 1) |
| 4F | 0.000596 (n = 1) | 0.0848 (n = 1) | 0.0543 (n = 1) |

*tested as the free base
n = the number of samples tested

Selected compounds were then tested in vivo using one or more of the functional assays described in the Biological Functional Assays section below.

In Vivo Biological Assays

Food Intake

The following screen is used to evaluate the efficacy of test compounds for inhibiting food intake in Sprague-Dawley rats after an overnight fast.

Male Sprague-Dawley rats were obtained from Charles River Laboratories, Inc. (Wilmington, Mass.). The rats are individually housed and fed powdered chow. They are maintained on a 12 hour light/dark cycle and received food and water ad libitum. The animals are acclimated to the vivarium for a period of one week before testing is conducted. Testing is completed during the light portion of the cycle.

To conduct the food intake efficacy screen, rats are transferred to individual test cages without food the afternoon prior to testing, and the rats are fasted overnight. After the overnight fast, rats are dosed the following morning with vehicle or test compounds. A known antagonist is dosed (3 mg/kg) as a positive control, and a control group receives vehicle alone (no compound). The test compounds are dosed at ranges between 0.1 and 100 mg/kg depending upon the compound. The standard vehicle is 0.5% (w/v) methylcellulose in water and the standard route of administration is oral. However, different vehicles and routes of administration are used to accommodate various compounds when required.

Food is provided to the rats 30 minutes after dosing and the Oxymax automated food intake system (Columbus Instruments, Columbus, Ohio) is started. Individual rat food intake is recorded continuously at 10-minute intervals for a period of two hours. When required, food intake is recorded manually using an electronic scale; food is weighed every 30 minutes after food is provided up to four hours after food is provided. Compound efficacy is determined by comparing the food intake pattern of compound-treated rats to vehicle and the standard positive control.

Oxygen Consumption

Whole body oxygen consumption is measured using an indirect calorimeter (Oxymax from Columbus Instruments, Columbus, Ohio) in male Sprague Dawley rats (if another rat strain or female rats is used, it will be specified). Rats (300-380 g body weight) are placed in the calorimeter chambers and the chambers are placed in activity monitors. These studies are done during the light cycle. Prior to the measurement of oxygen consumption, the rats are fed standard chow ad libitum. During the measurement of oxygen consumption, food is not available. Basal pre-dose oxygen consumption and ambulatory activity are measured every 10 minutes for 2.5 to 3 hours. At the end of the basal pre-dosing period, the chambers are opened and the animals are administered a single dose of compound (the usual dose range is 0.001 to 10 mg/kg) by oral gavage (or other route of administration as specified, i.e. s.c., i.p., i.v.). Drugs are prepared in methylcellulose, water or other specified vehicle (examples include PEG400, 30% beta-cyclo dextran and propylene glycol). Oxygen consumption and ambulatory activity are measured every 10 minutes for an additional 1-6 hours post-dosing.

The Oxymax calorimeter software calculates the oxygen consumption (ml/kg/h) based on the flow rate of air through the chambers and difference in oxygen content at inlet and output ports. The activity monitors have 15 infrared light beams spaced one inch apart on each axis, ambulatory activity is recorded when two consecutive beams are broken and the results are recorded as counts.

Resting oxygen consumption, during pre- and post-dosing, is calculated by averaging the 10-minute $O_2$ consumption values, excluding periods of high ambulatory activity (ambulatory activity count>100) and excluding the first 5 values of the pre-dose period and the first value from the post-dose period. Change in oxygen consumption is reported as percent and is calculated by dividing the post-dosing resting oxygen consumption by the pre-dose oxygen consumption *100. Experiments will typically be done with n=4-6 rats and results reported are mean+/−SEM. An increase in oxygen consumption of >10% is considered a positive result. Historically, vehicle-treated rats have no change in oxygen consumption from pre-dose basal.

Pharmacokinetic Experiment

A representative compound of the present invention (Example 1A) and a comparator compound (Example 2A) were individually dosed into two different male JVC/CAC rats at 1 mg/kg in a 10% ethanol and 90% (30% beta-cyclodextrin sulfobutylether) vehicle. Blood was subsequently collected at 0.083, 0.25, 0.5, 1, 2, 4, 6, 8 and 20 hours post IV administration. After spinning the blood samples down to get plasma, the plasma concentrations were determined by LC/MS/MS. The pharmacokinetic (PK) analysis was determined by inputting the resultant time concentration data into a Watson™ Laboratory Information Management System (LIMS).

The average clearance for the comparator compound (Example 2A) was very high at 361 mL/minute/kg, approximately 5 times hepatic blood flow. The half-life was very short at 0.7 hours, and the volume of distribution was high at 10 L/kg. Unlike the comparator compound, the compound of Example 1A had a moderate PK profile. The clearance was 18.6 mL/minute/kg, the half-life was 2.9 hours, and the volume of distribution was 2 L/kg. Clearly, the compound of the present invention (Example 1A) provides a better PK profile than the comparator compound (Example 2A) which would translate into a lower dose.

The invention claimed is:

1. A compound of Formula (I)

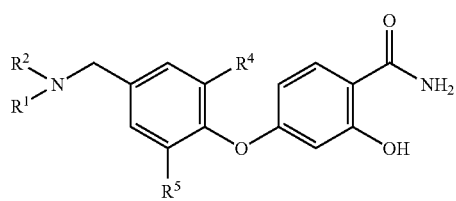

wherein:
R$^1$ is hydrogen or methyl;
R$^2$ is (C$_3$-C$_{10}$)alkyl, 5-6 membered cycloalkyl optionally fused to a benzene ring, or —(CH(R))$_m$(CH$_2$)$_n$-A, where m is 1; n is 0, 1 or 2; R is hydrogen, methyl or ethyl; and A is (C$_1$-C$_4$)alkoxy, phenoxy, phenyl, 3-8 membered cycloalkyl, 5-6 membered heterocycle containing 1 to 2 heteroatoms independently selected from O, N, or S, or 5-6 membered heteroaryl containing 1 to 3 heteroatoms independently selected from O, S, or N; and where said phenyl, said cycloalkyl, said heterocycle, and said heteroaryl are optionally fused to a benzene ring or optionally substituted with one to three substituents independently selected from —OH, halo, (C$_1$-C$_4$)alkyl, —CF$_3$, —OCF$_3$, (C$_1$-C$_4$)alkoxy, CN, acetylamino, or phenoxy;
R$^4$ is hydrogen or halo; and
R$^5$ is hydrogen or halo;
or a pharmaceutically acceptable salt thereof.

2. The compound of claim 1 wherein:
R$^1$ is hydrogen;
R$^2$ is (C$_4$-C$_{10}$)alkyl;
R$^4$ is hydrogen or fluoro; and
R$^5$ is hydrogen or fluoro;
or a pharmaceutically acceptable salt thereof.

3. The compound of claim 1 selected from the group consisting of:
4-{2-Fluoro-4-[(3-methyl-butylamino)-methyl]-phenoxy}-2-hydroxy-benzamide; and
4-{2,6-Difluoro-4-[(3-methyl-butylamino)-methyl]-phenoxy}-2-hydroxy-benzamide;
or a pharmaceutically acceptable salt thereof.

4. The compound of claim 1 wherein:
R$^1$ is hydrogen;
R$^2$ is 5-6 membered cycloalkyl optionally fused to a benzene ring;
R$^4$ is hydrogen or fluoro; and
R$^5$ is hydrogen or fluoro;
or a pharmaceutically acceptable salt thereof.

5. The compound of claim 1 selected from the group consisting of:
4-[2-Fluoro-4-(indan-2-ylaminomethyl)-phenoxy]-2-hydroxy-benzamide;
4-(4-Cyclohexylaminomethyl-2,6-difluoro-phenoxy)-2-hydroxy-benzamide; and
4-[2,6-Difluoro-4-(indan-2-ylaminomethyl)-phenoxy]-2-hydroxy-benzamide;
or a pharmaceutically acceptable salt thereof.

6. The compound of claim 1 wherein:
R$^1$ is hydrogen;
R$^2$ is —(CH(R))$_m$(CH$_2$)$_n$-A, where m is 1, n is 0, and A is 3-6 membered cycloalkyl, pyridinyl, or 5-6 membered heterocycle containing 1 to 2 heteroatoms independently selected from O, S, or N, where said cycloalkyl and said heterocycle are optionally substituted with hydroxy;
R$^4$ is hydrogen or fluoro; and
R$^5$ is hydrogen or fluoro;
or a pharmaceutically acceptable salt thereof.

7. The compound of claim 1 selected from the group consisting of:
4-(2-Fluoro-4-{[(tetrahydro-furan-2-ylmethyl)-amino]-methyl}-phenoxy)-2-hydroxy-benzamide;
4-(2-Fluoro-4-{[(tetrahydro-pyran-4-ylmethyl)-amino]-methyl}-phenoxy)-2-hydroxy-benzamide;
4-(2-Fluoro-4-{[(1-hydroxy-cyclohexylmethyl)-amino]-methyl}-phenoxy)-2-hydroxy-benzamide;
4-(2,6-Difluoro-4-{[(tetrahydro-furan-2-ylmethyl)-amino]-methyl}-phenoxy)-2-hydroxy-benzamide;
4-(2,6-Difluoro-4-{[(1-hydroxy-cyclohexylmethyl)-amino]-methyl}-phenoxy)-2-hydroxy-benzamide; and
4-{2-Fluoro-4-[((R)-1-pyridin-2-yl-propylamino)-methyl]-phenoxy}-2-hydroxy-benzamide;
or a pharmaceutically acceptable salt thereof.

8. The compound of claim 1 wherein:
R$^1$ is hydrogen;
R$^2$ is —(CH(R))$_m$(CH$_2$)$_n$-A, where m is 1, n is 1, and A is (C$_1$-C$_4$)alkoxy, phenoxy, 3-6 membered cycloalkyl, or 5-6 membered heterocycle containing 1 to 2 heteroatoms independently selected from O, S, or N;
R$^4$ is hydrogen or fluoro;
R$^5$ is hydrogen or fluoro; and
or a pharmaceutically acceptable salt thereof.

9. The compound of claim 1 selected from the group consisting of:
4-{4-[(2-Cyclopropyl-ethylamino)-methyl]-2-fluoro-phenoxy}-2-hydroxy-benzamide;
4-{2-Fluoro-4-[(2-phenoxy-ethylamino)-methyl]-phenoxy}-2-hydroxy-benzamide;
4-{2-Fluoro-4-[(2-isopropoxy-ethylamino)-methyl]-phenoxy}-2-hydroxy-benzamide;
4-{4-[(2-Cyclopropyl-ethylamino)-methyl]-2,6-difluoro-phenoxy}-2-hydroxy-benzamide; and
4-(2,6-Difluoro-4-{[2-(tetrahydro-pyran-4-yl)-ethylamino]-methyl}-phenoxy)-2-hydroxy-benzamide;
or a pharmaceutically acceptable salt thereof.

10. The compound of claim 1 which is the hydrochloride salt of 4-{4-[(2-cyclopropyl-ethylamino)-methyl]-2-fluoro-phenoxy}-2-hydroxy-benzamide.

11. A compound having the following formula

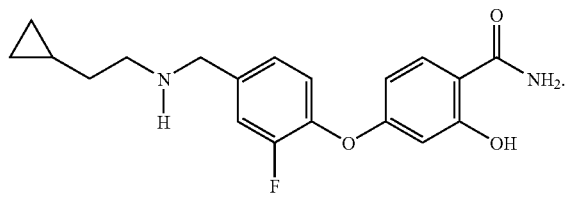

12. A pharmaceutically acceptable salt of the compound of claim 11.

13. A pharmaceutical composition comprising (i) a therapeutically effective amount of a compound or a pharmaceutically acceptable salt thereof of claim 1; and (ii) at least one a pharmaceutically acceptable excipient, diluent, or carrier.

14. The composition of claim 13 further comprising at least one additional pharmaceutical agent.

15. The composition of claim 14 wherein said at least one additional pharmaceutical agent is an anti-obesity agent.

16. The composition of claim 15 wherein said anti-obesity agent is selected from the group consisting of:

apo-B/MTP inhibitors, cannabinoid-1 (CB-1) receptor antagonists or inverse agonists, 11β-hydroxy steroid dehydrogenase-1 (11β-HSD type 1) inhibitors, peptide $YY_{3-36}$, MCR-4 agonists, CCK-A agonists, monoamine reuptake inhibitors, sympathomimetic agents, $β_3$ adrenergic agonists, dopamine agonists, melanocyte-stimulating hormone analogs, 5-HT2c agonists, melanin concentrating hormone antagonists, leptin, leptin analogs, leptin agonists, galanin antagonists, lipase inhibitors, bombesin agonists, neuropeptide-Y antagonists, thyromimetic agents, dehydroepiandrosterone or analogs thereof, glucocorticoid antagonists, orexin antagonists, glucagon-like peptide-1 agonists, ciliary neurotrophic factors, human agouti-related protein antagonists, ghrelin antagonists or inverse agonists, histamine 3 antagonists or inverse agonists, and neuromedin U agonists.

* * * * *